(12) United States Patent
Redmond et al.

(10) Patent No.: US 6,613,070 B2
(45) Date of Patent: Sep. 2, 2003

(54) SYSTEM AND METHOD FOR SEALING VASCULAR PENETRATIONS WITH HEMOSTATIC GELS

(75) Inventors: Russell J. Redmond, Goleta, CA (US); Claude Vidal, Santa Barbara, CA (US); Cary J. Reich, Los Gatos, CA (US); Felix Vega, San Francisco, CA (US); Michael Collinson, Goleta, CA (US); Joseph F. Rondinone, Los Gatos, CA (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 09/882,296

(22) Filed: Jun. 14, 2001

(65) Prior Publication Data

US 2002/0006429 A1 Jan. 17, 2002

Related U.S. Application Data

(63) Continuation-in-part of application No. 09/361,663, filed on Jul. 27, 1999, now Pat. No. 6,334,865.
(60) Provisional application No. 60/095,306, filed on Aug. 4, 1998, and provisional application No. 60/212,181, filed on Jun. 16, 2000.

(51) Int. Cl.[7] .............................................. A61B 17/08
(52) U.S. Cl. ...................................... 606/213; 606/139
(58) Field of Search ................................. 606/213, 214, 606/139

(56) References Cited

U.S. PATENT DOCUMENTS

| | | |
|---|---|---|
| 4,744,364 A | 5/1988 | Kensey |
| 4,890,612 A | 1/1990 | Kensey |
| 5,108,421 A | 4/1992 | Fowler |
| 5,221,259 A | 6/1993 | Weldon et al. |
| 5,330,446 A | 7/1994 | Weldon et al. |
| 5,370,660 A | 12/1994 | Weinstein et al. |
| 5,383,896 A | 1/1995 | Gershony et al. |
| 5,413,571 A | 5/1995 | Katsaros et al. |
| 5,419,765 A | 5/1995 | Weldon et al. |
| 5,486,195 A | 1/1996 | Myers et al. |
| 5,591,205 A | 1/1997 | Fowler |
| 5,626,601 A | 5/1997 | Gershony et al. |
| 5,653,730 A | 8/1997 | Hammerslag |
| 5,728,132 A | 3/1998 | Van Tassel et al. |
| 5,752,974 A | 5/1998 | Rhee et al. |
| 5,855,559 A | 1/1999 | Van Tassel et al. |
| 6,045,570 A | 4/2000 | Epstein et al. |
| 6,123,667 A | 9/2000 | Poff et al. |
| 6,193,670 B1 | 2/2001 | Van Tassel et al. |

FOREIGN PATENT DOCUMENTS

EP        0493810     11/1995

*Primary Examiner*—Gary Jackson
(74) *Attorney, Agent, or Firm*—Townsend and Townsend and Crew LLP

(57) ABSTRACT

Systems and method for sealing vascular penetrations rely on placement of a temporary barrier on the posterior side of the penetration. Penetrations are then sealed by delivering a hemostatic gel to a region over the penetration, where the barrier both inhibits loss of the gel and promotes back flow of blood into the gel. A combination of natural clotting factors in the blood and hemostatic agents in the gel promote rapid and effective sealing of the vascular penetration. Specific systems for performing the method include a barrier carrier for temporary placement of the barrier within the blood vessel and a gel delivery tube which may be positioned within a tissue tract or line of penetration simultaneously with the barrier carrier to deliver the hemostatic gel.

23 Claims, 21 Drawing Sheets

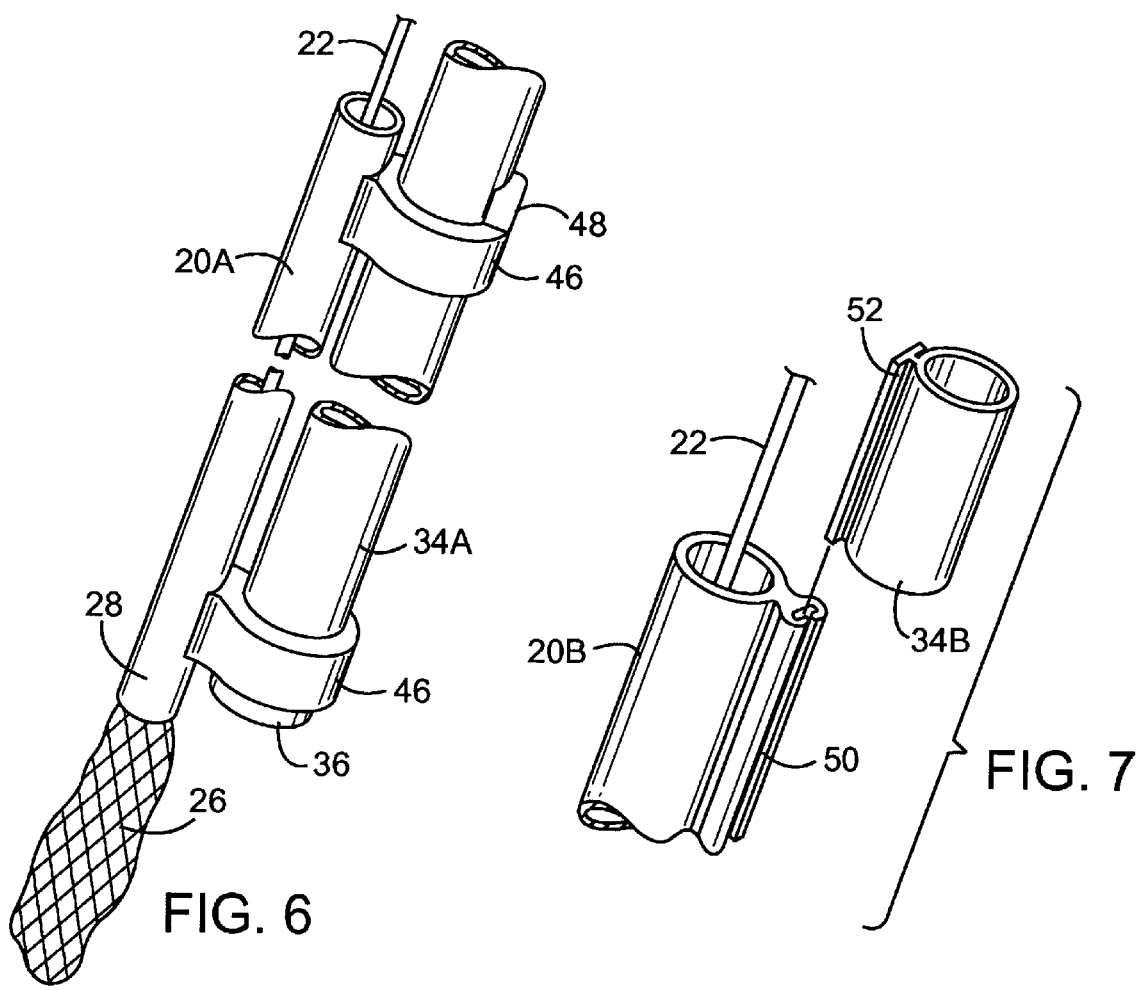
FIG. 6
FIG. 7
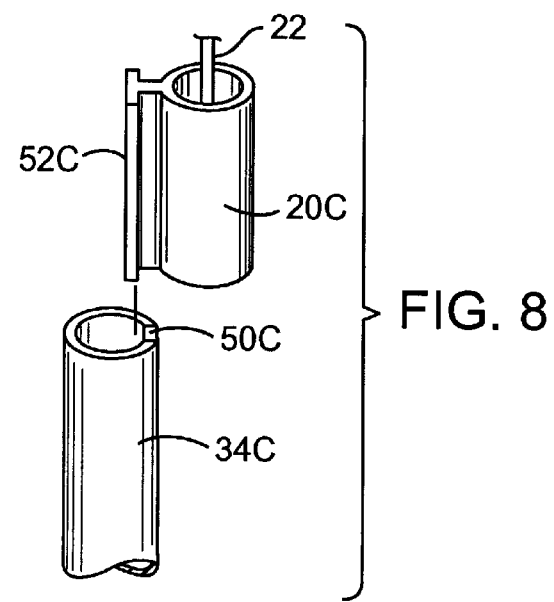
FIG. 8

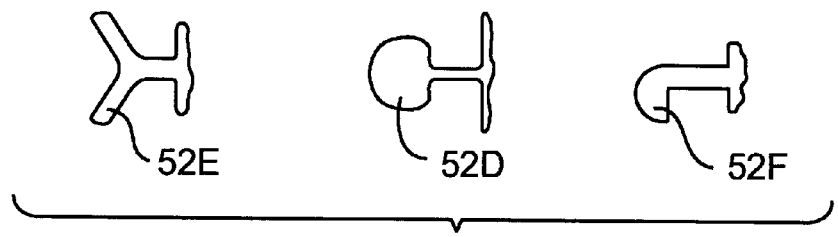
FIG. 9
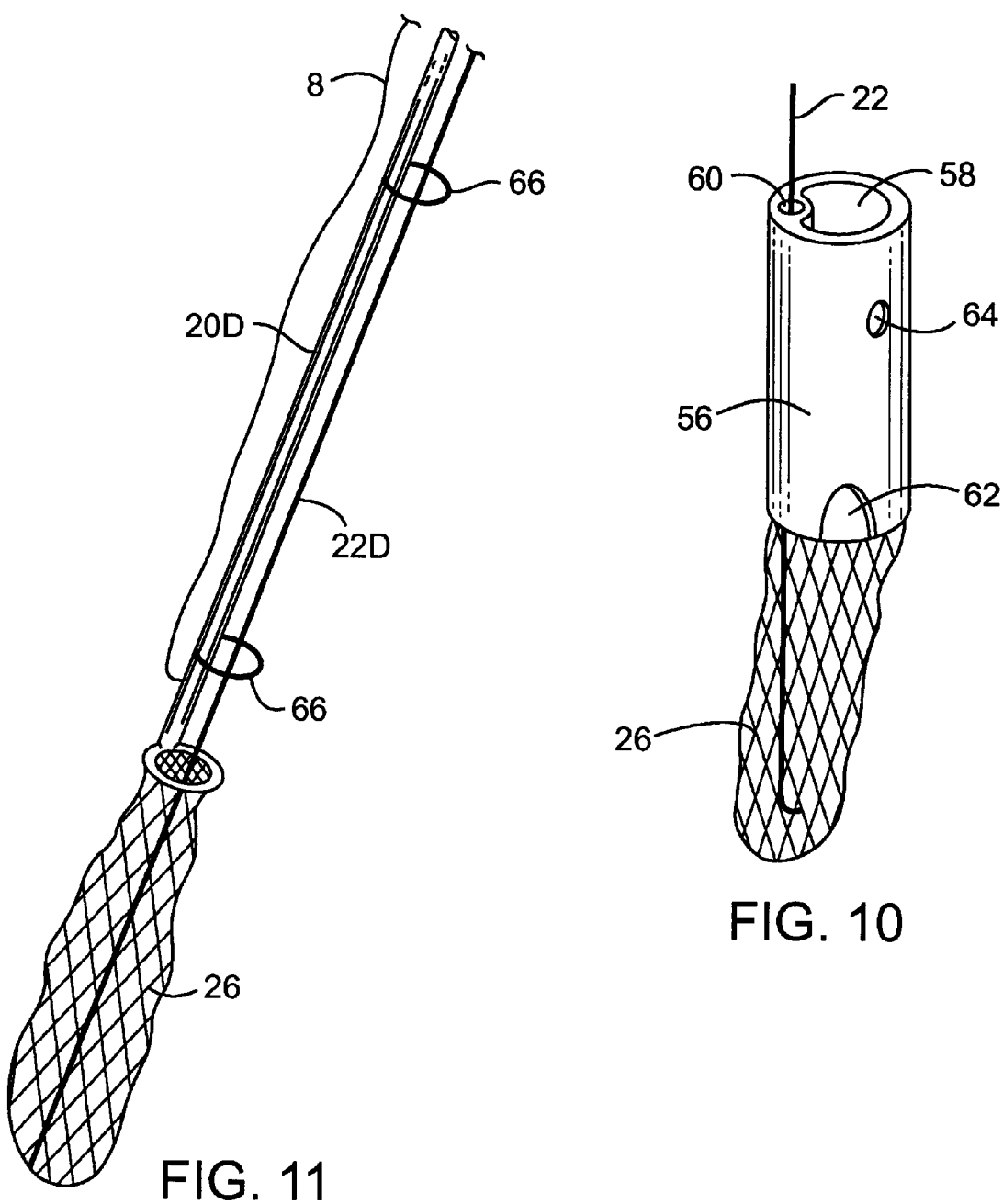
FIG. 10
FIG. 11

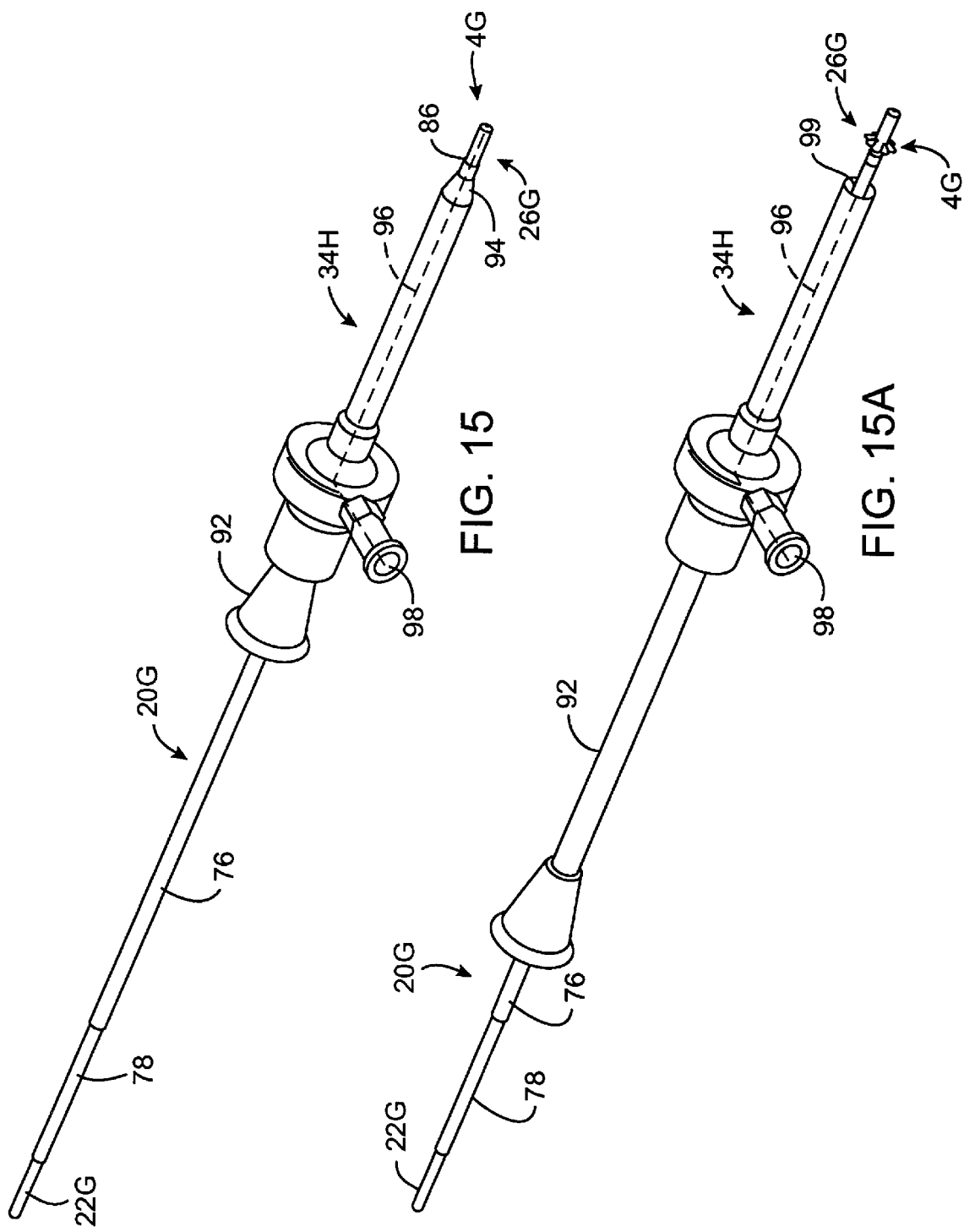

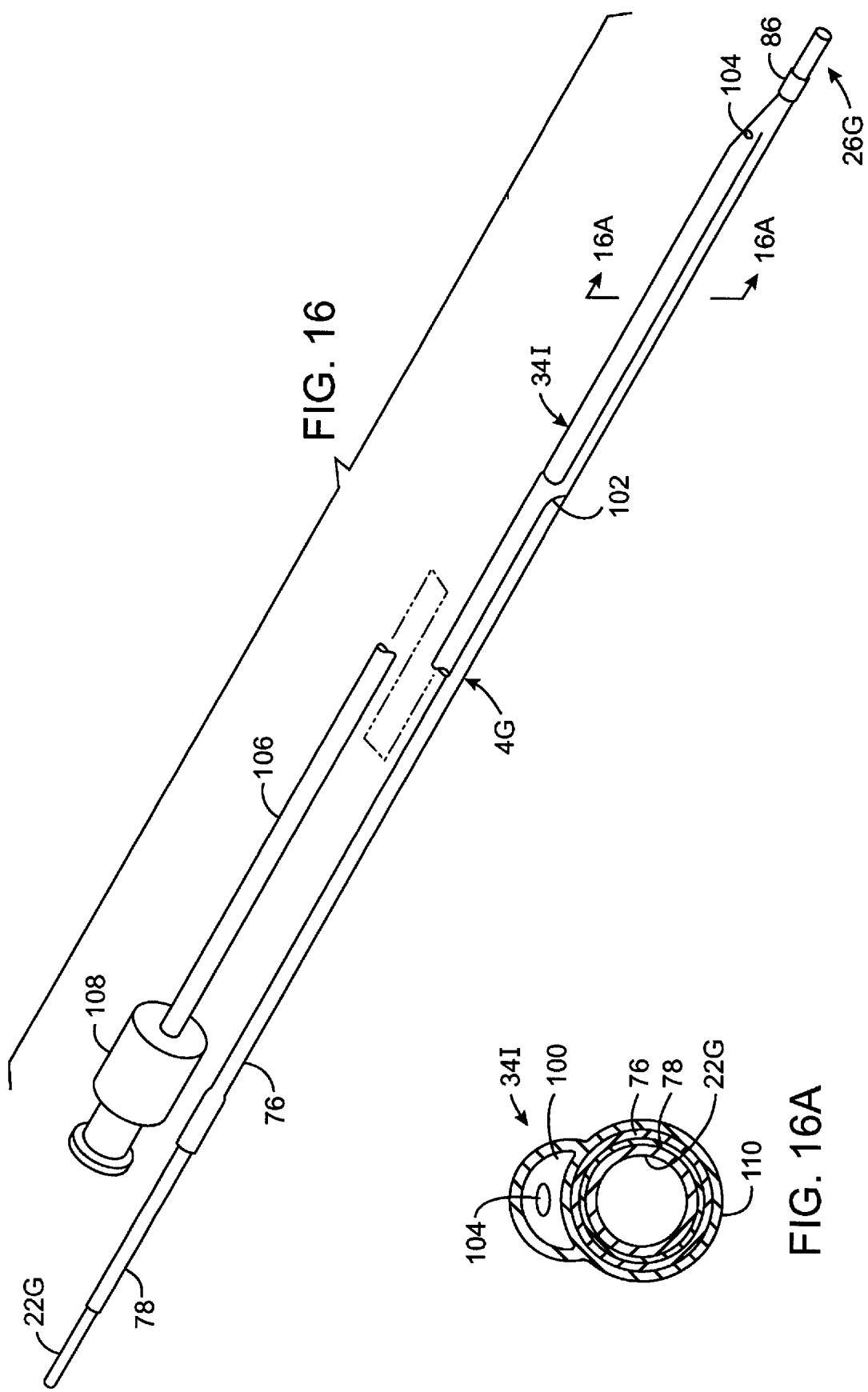

SYSTEM AND METHOD FOR SEALING VASCULAR PENETRATIONS WITH HEMOSTATIC GELS

CROSS-REFERENCE TO RELATED APPLICATIONS

This application claims the benefit of Provisional Patent Application No. 60/212,181, filed on Jun. 16, 2000, the full benefit of which is incorporated herein by reference. This application is also a continuation-in-part of application Ser. No. 09/361,663, filed on Jul. 27, 1999, now U.S. Pat. No. 6,334,865 which claimed the benefit of Provisional Patent Application No. 60/095,306, filed on Aug. 4, 1998, the full disclosures of which are incorporated herein by reference.

BACKGROUND OF THE INVENTION

1. Field of the Invention

Various therapeutic and diagnostic medical procedures involve accessing a vein or artery through a percutaneous tissue track. Femoral arteries are commonly accessed during various procedures, such as angiograms, angioplasties, catheterization and peripheral artery angioplasty. Accessing the blood vessel typically includes insertion of a relatively large diameter introducer sheath along the percutaneous tissue track and into an access opening in the blood vessel. Medical instruments, including guidewires and various catheters, are then introduced into the patient's vascular system through the introducer sheath.

At the conclusion of the medical procedure, the introducer sheath is removed leaving a relatively large access opening in the vessel wall which must be closed to stop bleeding. This has been traditionally accomplished through the use of digital pressure at the puncture site. This, however, requires that direct pressure be applied for an extended period of time, such as 45 minutes to an hour, to effectively stop bleeding from the access opening. Mechanical substitutes for finger pressure have been used, but can be uncomfortable for the patient. Using digital pressure to stop bleeding is not only expensive from the standpoint of the time of the trained medical person applying the pressure, it is also quite physically difficult to maintain a constant pressure at the puncture site for such an extended period. In addition, applying direct pressure to the puncture site causes the vessel being accessed to be blocked which can create its own problems, such as ischemia.

An early alternative to direct pressure to stop bleeding from an access opening in a blood vessel was the use of biodegradable collagen plugs. These plugs are either applied directly on top of the puncture site in the vessel wall, or are secured to the wall with a suture and polymer anchor. In the latter device, the polymer anchor is placed within the artery, against the inner wall of the artery. While such devices worked, the plug and/or anchors could cause complications.

In lieu of applying direct pressure to the puncture site, tissue glues and hemostatic materials have been used to halt blood flow from the blood vessel access opening. These materials are typically positioned along the percutaneous tissue track using a balloon catheter, the balloon being situated at the distal end of the catheter within the blood vessel. When the balloon is inflated, it effectively seals the opening in the blood vessel to permit the hemostatic material to be properly positioned at the access opening in the blood vessel without being introduced into the vessel. After a period of time, the balloon is deflated and the balloon catheter is withdrawn from the blood vessel and tissue track. These devices require a very small balloon and can be expensive.

For these reasons, it would be desirable to provide improved systems and methods for sealing vascular penetrations, such as vascular penetrations in the femoral artery, after performing various intravascular procedures such as angiography, angioplasty, stent placement, aneurysm treatment, and the like. It would be particularly beneficial to provide methods and systems which could reliably seal such vascular penetration sites using materials which would be substantially or completely resorbed over time, thus reducing the risk of complications associated with implantation of materials at the penetration site. It would still further be desirable to provide methods and systems which promote natural healing of the vascular penetration site and associated tissue tract through the activation and stimulation of the clotting cascade at the region of vascular penetration. At least several of these objectives will be met by the inventions described hereinafter.

2. Description of the Background Art

Methods and systems for delivering hemostatic agents to blood vessel penetrations are described in U.S. Pat. Nos. 6,193,670; 6,045,570; 5,855,559; and 5,728,132. A device employing an articulated foot for suturing vascular penetrations is described in U.S. Pat. Nos. 5,752,979; 5,653,730; 5,626,601; 5,591,205; 5,486,195; 5,419,765; 5,413,571; 5,383,896; 5,370,660; 5,330,446; 5,221,259; 4,744,364; and European Patent 493 810B1.

SUMMARY OF THE INVENTION

The present invention provides systems and methods for delivering a flowable hemostatic gel to an outside (anterior) side of a vascular penetration. The vascular penetration is typically positioned at the distal or remote end of a tissue tract which has been formed to provide access to the underlying blood vessel, typically a femoral or other artery which has been accessed in order to perform an intravascular procedure, such as angiography, angioplasty, stent placement, aneurysmal repair, neurological interventions, intravascular cardiac bypass, or other cardiac and peripheral vascular procedures which are known in the art or may be devised in the future. In general, both the systems and the methods rely on the positioning of a barrier on an inside (posterior) side of the blood vessel penetration in order to provide a temporary seal of the penetration. After the barrier is in place, the flowable hemostatic gel will be delivered over the barrier to a region directly over the anterior side of the vascular penetration. The barrier will be able to contain the flowable hemostatic gel, substantially inhibiting or preventing any leakage, migration, or intrusion of the gel into the underlying blood vessel lumen. The barrier, however, will also permit the passage of a controlled amount of blood from the blood vessel back into the tissue tract where it can combine with the hemostatic gel to promote coagulation of the gel and healing of the vascular penetration and tissue tract. After the hemostatic gel has been delivered and "set," typically taking from one to several minutes, the barrier will be removed, leaving the gel in place to continue coagulation and healing of the penetration. In particular, after the relative short setting period, the gel will be sufficiently solidified to inhibit or prevent back bleeding into the tissue tract, thus reducing or eliminating the need to apply pressure to the penetration.

Suitable hemostatic gels will comprise a biologically compatible matrix, typically a cross-linked protein, such as gelatin, collagen, albumin, or the like, which is hydrated or hydratable to form the structural component of the gel over the vascular penetration as described above. The hemostatic gel will typically also include an active component, usually a protein involved in the clotting cascade, most usually being thrombin, to promote clotting of the gel when exposed to blood. A particularly suitable flowable gel is described in U.S. Pat. Nos. 6,063,061 and 6,066,325, assigned to the Assignee of the present application, the full disclosures of which are incorporated herein by reference. Suitable materials as described in these patents are commercially available under the trade name FloSeal™ from Fusion Medical Technologies, Inc., the Assignee of the present Application. Other suitable plug-forming materials include glues or sealants comprising naturally occurring coagulation proteins, such as fibrinogen and/or thrombin, or commercially available synthetic solvents, such as those available under the tradenames Coseal™ and Focalseal™.

The vascular penetrations to be sealed may be formed by any conventional access technique, such as the Seldinger technique where the tissue tract and vascular penetration are first formed using a needle and subsequently dilated using a suitable dilation cannula. The tissue tracts will thus pass through a layer of muscle tissue overlying the target blood vessel. In the case of the femoral artery, access will usually be gained through the patient's groin where the length of the tissue tract is typically from 5 to 20 cm, depending on the size of the patient and angle at which the artery is approached. Penetration through the blood vessel will have an outside, i.e. a side adjacent to the distal or remote end of the tissue tract, and an inside, i.e. a side which is within the blood vessel. As described above, the flowable hemostatic gel of the present invention will be delivered to a region which generally overlies the outside of the blood vessel penetration.

In order to deliver the flowable hemostatic gel to the outside side of the vascular penetration without significant passage of the gel into the blood vessel lumen, a barrier is placed across the side of the penetration located on the inside of the blood vessel. The barrier may be any structure which will inhibit or prevent the flow, migration, or intrusion of the gel into the blood vessel lumen. The structure of the barrier must be suitable for delivery through the tissue tract and subsequent deployment across the vascular penetration. The first type of barrier may comprise a flexible element, such as a semipermeable membrane, mesh, mallecott structure, or the like. Such structures will be porous or foramenous with pore or aperture sizes selected to permit blood flow out of the blood vessel while inhibiting the passage of the gel into the blood vessel. Alternatively, the barriers can be solid and/or rigid non-porous structures having one or several discrete passages therethrough which are sized to permit blood flow while inhibiting the passage of the flowable gel into the blood vessel. In an exemplary embodiment, the barrier is a solid articulated foot (as described in detail below) having a single circular aperture with a diameter of about 0.1 mm.

In a first specific aspect, the present invention provides a system for delivering the flowable gel comprising an elongate barrier carrier in a delivery tube. The elongate barrier carrier is positionable through the tissue tract and includes the deployable barrier attached at or near its distal end. The barrier may be any of the barriers described above. The delivery tube is positionable in the tissue tract simultaneously with the elongate barrier carrier and includes a passage for delivery of the hemostatic gel to the outside of the vascular penetration. The passage is typically an elongate lumen within the delivery tube, and the delivery tube can be configured to lie in parallel with the elongate barrier carrier, coaxially over the elongate barrier carrier, or preferably coaxially within the central lumen of the elongate barrier carrier.

The barrier carrier will typically include a mechanism for deploying the barrier, i.e. expanding, extending, or positioning the carrier across the inside of the vascular penetration. Particular examples of the barrier and deployment mechanism comprise generally tubular mesh which can be axially contracted to cause radial expansion, as generally shown in FIGS. 1–4, 6, and 11–12 hereinafter. Alternatively, the barrier can be mallecott-type structure as shown in FIGS. 13A, 13B, 14 and 14B. In a presently preferred embodiments, the barrier is generally a solid foot which is pivotally attached to a shaft to permit deployment within the blood vessel, as illustrated in FIGS. 17–20 and 22–28 hereinafter.

In the second aspect of the system of the present invention, the delivery tube may include a blood reservoir which collects blood with a distal end of the delivery tube as positioned in the lumen of the blood vessel. The presence of blood in the reservoir will be visually discernable so that entry of the distal end of the delivery tube into the blood vessel can be confirmed. Usually, the reservoir will include a resiliently expandable structure which permits filling of the reservoir at arterial blood pressures which will empty the reservoir at pressures below arterial blood pressure. The presence of such a structure provides certain advantages. The first advantage is that, while the distal end of the delivery tube lies within the blood vessel, the amount of blood in the reservoir will vary as a result of the natural pulsation of arterial pressure, e.g. between 30 mm Hg to about 120 mm Hg. Accidental or intentional removal of the distal of the delivery tube from the blood vessel lumen will cause such pulsation's to cease and eventually permit the resilient structure to return the blood to the tissue tract at the point where the distal end of the delivery tube is positioned. The latter return of blood can be advantageous when combined with delivery of the hemostatic agent, where the blood can provide an initial bolus of blood to initiate clotting with the hemostatic gel.

In a still further aspect of the present invention, methods for delivering the hemostatic gel to the outside of the vascular penetration comprise positioning the barrier on the inside of the vascular penetration and delivering the flowable hemostatic gel to the anterior side of the penetration. The barrier may be any of the barriers described above which inhibit passage of the hemostatic gel into the blood vessel lumen but permit the flow of blood back into the tissue tract to promote clotting in the presence the hemostatic gel. The methods may further comprise collecting blood through the tissue tract prior to delivering the flowable hemostatic gel and thereafter combining the collected blood with the hemostatic gel to promote clotting. Such methods may be performed using the apparatus having the blood collection reservoirs described above. The positioning step may comprise positioning a semipermeable membrane or other porous or foramenous structure as described above, or may comprise positioning a solid barrier having at least one passage therethrough, also as described above. The flowable gel will typically comprise at least one member of the clotting cascade, typically thrombin. Gels will usually comprise a collagen or gelatin gel matrix, as described above.

BRIEF DESCRIPTION OF THE DRAWINGS

FIG. 6 illustrates an alternative embodiment of the invention in which the thread-type delivery tube alignment device of FIGS. 1–5 has been replaced by guides positioned along the barrier carrier which engage the delivery tube, the delivery tube including a stop to properly position the open distal end of the delivery tube relative to the distal end of the barrier carrier;

FIGS. 7 and 8 illustrate further alternative embodiments of the invention in which the barrier sheath and delivery tube include slides and slide openings to guide the delivery tube along the barrier sheath;

FIG. 9 illustrates three alternative embodiments of differently shaped slides which could be used with the embodiments of FIGS. 7 and 8;

FIG. 10 illustrates a further embodiment of the invention in which the barrier carrier and delivery tube are combined into a single structure including a main lumen, through which the flowable material passes, and a supplemental lumen, through which the barrier actuator passes, the combination tube having a number of flowable material exits at the distal end of the combination tube and along the length of the combination tube;

FIG. 11 illustrates an alternative embodiment of the barrier assembly of FIG. 2 in which the barrier sheath has been replaced by a solid barrier carrier with the barrier actuator being external of the barrier carrier and guided along the barrier carrier by several guide loops;

FIG. 15 illustrates the barrier assembly of FIG. 14 with a further embodiment of a delivery tube mounted over the barrier carrier of the barrier assembly;

FIG. 15A illustrates the device of FIG. 15 with the spacer tube retracted opening up an annular flowable material path between the delivery tube and the barrier sheath;

FIG. 16 illustrates a further embodiment of the invention in which the barrier assembly of FIG. 14 has a laterally-collapsible flowable material delivery tube mounted to it; and FIG. 16A is a cross-sectional view taken along line 16A—16A of FIG. 16 with the delivery tube in an expanded condition.

FIG. 18A illustrates the foot in its generally deployed configuration which would be suitable for placement within the blood vessel to cover the posterior side of the vascular penetration, while FIG. 18B illustrates the foot in a low profile configuration suitable for introducing and removing the foot from the blood vessel.

DESCRIPTION OF THE SPECIFIC EMBODIMENTS

Figure 4:
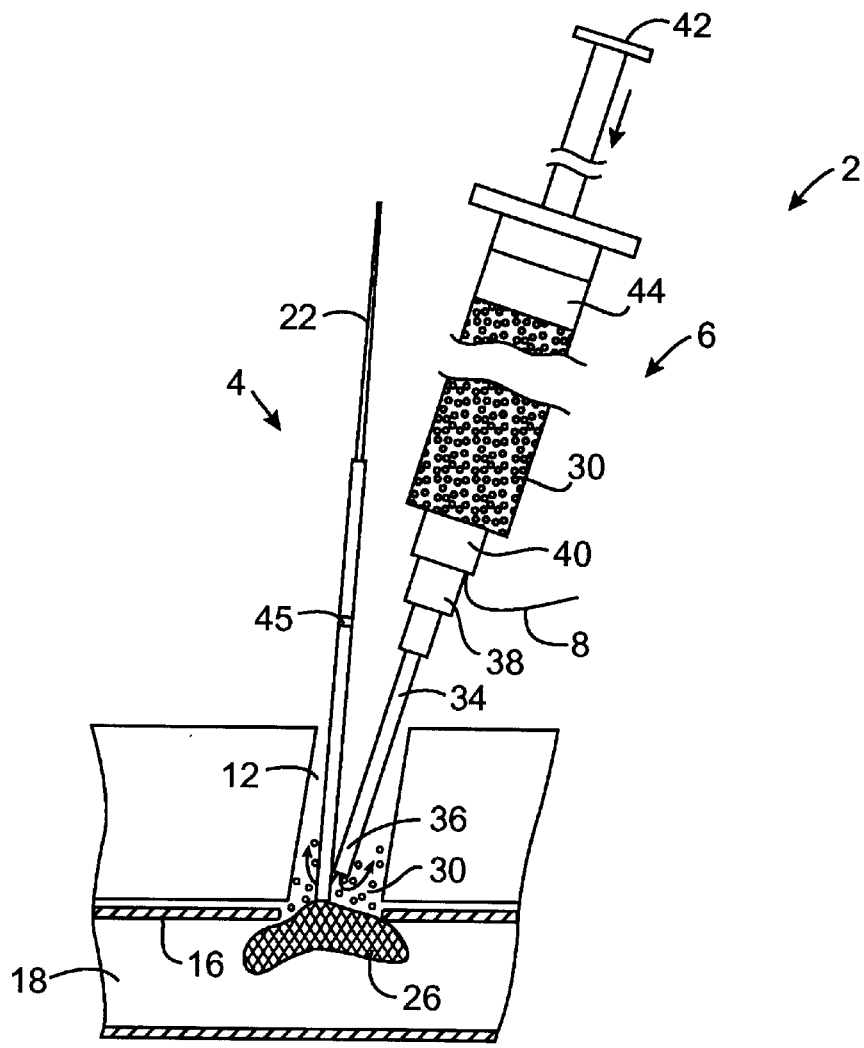
FIG. 4 illustrates a percutaneous tissue track closure assembly made according to the invention showing the barrier actuator extending from the open proximal end of the barrier sheath, a syringe filled with a hemostatic flowable material secured to the Luer fitting at the proximal end of the delivery tube and the introduction of the hemostatic flowable material from the syringe through the open distal end of the delivery tube into the percutaneous tissue track with the hemostatic flowable material being prevented from entering the blood vessel by the deployed barrier.

Referring initially to FIG. 4, a percutaneous tissue track closure assembly 2 is seen to include a barrier assembly 4, a thread 8 and a flowable material assembly 6 coupled to and aligned with the barrier assembly 4 using thread 8. Thread 8 acts as an alignment device for properly positioning the barrier assembly and flowable material assembly relative to one another as will be described in more detail below.

Figure 1:
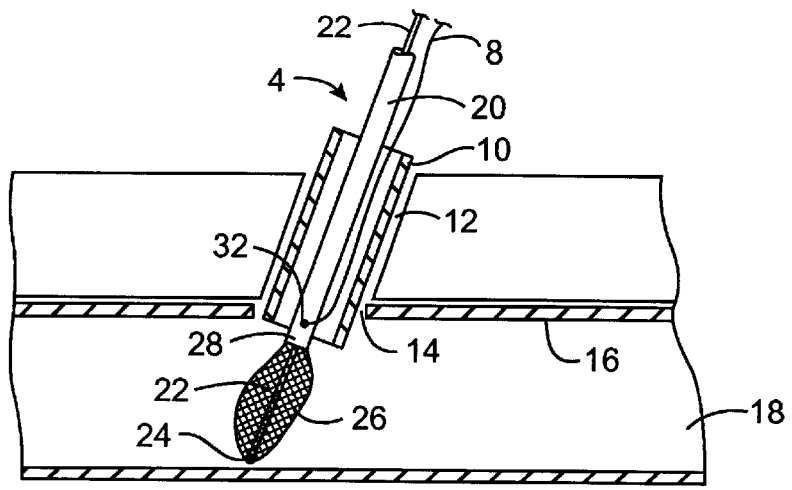
FIG. 1 illustrates an introducer catheter within a percutaneous tissue track and a barrier assembly passing through the introducer catheter with the semipermeable barrier within the blood vessel in its laterally retracted, undeployed configuration.

Referring now to FIG. 1, an introducer sheath 10 is shown extending along a percutaneous tissue track 12 and extending a short distance through an access opening 14 formed in the wall 16 of a blood vessel 18. Introducer sheath 10 had been used to introduce appropriate medical devices, such as guidewires and catheters, into blood vessel 18 during a prior therapeutic or diagnostic procedure. Before removing introducer sheath 10, the distal end of the barrier assembly 4 is passed through the introducer sheath.

Barrier assembly 4 includes a tubular barrier carrier 20 housing a flexible, wire-like barrier actuator 22 therein. The distal end 24 of barrier actuator 22 is secured to the center of a semipermeable barrier 26, the semipermeable barrier being connected to the distal end 28 of barrier carrier 20. Barrier 26 is constructed so that it can assume the laterally retracted, undeployed configuration of FIG. 1 or the laterally expanded, deployed configuration of FIG. 2 by either pushing or pulling on barrier actuator 22. Therefore, barrier actuator 22 is flexible but has sufficient columnar strength to move barrier 26 between the laterally expanded configuration of FIG. 2 and the laterally retracted configuration of FIG. 1. Barrier 26 is preferably a mesh-like material which permits a restricted flow of blood through the barrier but prevents a hemostatic flowable material 30, originally within syringe 6, from passing through barrier 26 and into blood vessel 18.

Figure 2:
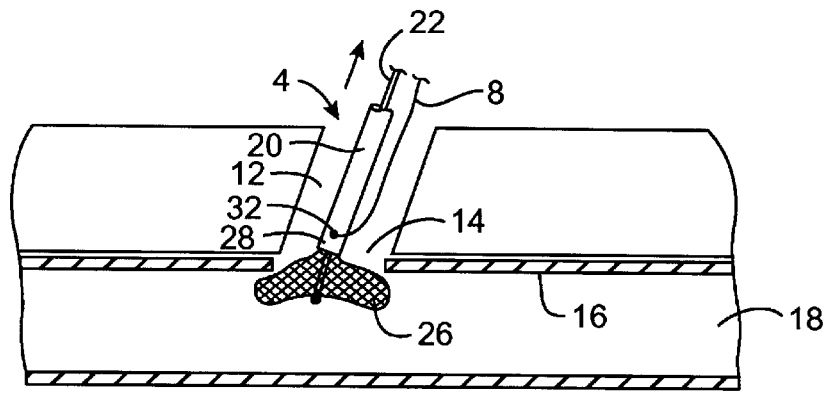
FIG. 2 is similar to FIG. 1, but with the introducer sheath removed from the percutaneous tissue track and the barrier in its laterally expanded, deployed configuration covering the access opening in the blood vessel.
Figure 3:
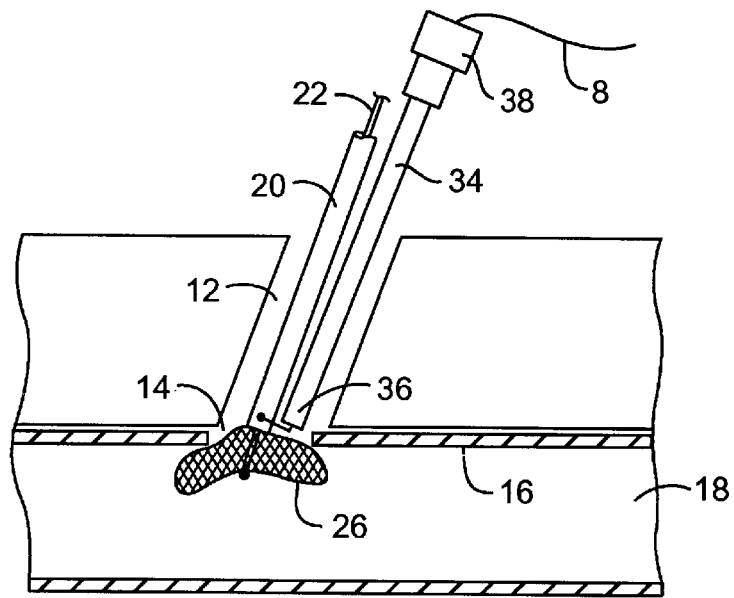
FIG. 3 shows a flowable material delivery tube passing over a thread extending from the distal end of the barrier sheath of FIG. 2, the distal end of the delivery tube being generally aligned with the attachment point of the thread to the barrier sheath.

FIG. 2 illustrates barrier assembly 4 within percutaneous tissue track 12 after barrier actuator 22 has been pulled to cause barrier 26 to be deformed into its laterally expanded, mushroom-like deployed configuration and introducer sheath 10 has been removed. FIG. 2 also illustrates thread 8 extending from a position 32 adjacent the distal end 28 of barrier carrier 20. FIG. 3 illustrates the placement of a flowable material delivery tube 34 over thread 8 until the open distal end 36 of tube 34, which acts as the delivery tube exit, is adjacent position 32 at the end of thread 8. As seen in FIG. 3, thread 8 extends out from the Luer fitting 38 at the proximal end of delivery tube 34. Luer fitting 38 is mounted to a Luer fitting 40 at the distal end of syringe 6. As shown in FIG. 4, thread 8 is captured between the Luer fittings 38, 40, thus securing open distal end 36 of delivery tube 34 adjacent position 32 along barrier carrier 20. At this point, the user depresses the thumb pad 42 of syringe 6 causing piston 44 to move distally in the direction of the arrow to force hemostatic flowable material 30 from syringe 6, through tube 34, out open distal end 36, and into tissue track 12.

FIG. 4 also shows alignment markings, indicators or indicia 45 on barrier carrier 20. Markings 45 can be used instead of or in addition to thread 8 as an alignment device. In FIG. 4, markings 45 are positioned to be aligned with the lower edge of Luer fitting 38 when distal end 36 is properly positioned.

Hemostatic flowable material 30 may be a material can form a plug, such as a fibrin glue, or a material which either swells upon contact with an aqueous liquid, such as blood or aqueous blood components, or causes blood or one or more blood components to clot upon contact with the hemostatic flowable material, and preferably both. In the preferred embodiment, hemostatic flowable material 30 includes a bioabsorbable, flowable, granular gel as described in U.S. patent application Ser. No. 09/032,370, filed Feb. 27, 1998; Ser. No. 08/903,674, filed Jul. 31, 1997; No. 60/050,437, filed Jun. 18, 1997; and Ser. No. 08/704,852, filed Aug. 27, 1996, entitled Fragmented Polymeric Compositions and Methods for Their Use. In addition, hemostatic flowable material 30 max include thrombin or thrombin and fibrinogen as the clotting agent. Flowable material delivery tube 34 is preferably at least a 16 gauge, and preferably a 15 gauge, tube. Flowable material 30 can also include other agents, such as antibacterial agents, antifibrinolytic agents, or bacteriostatic agents.

In many applications, percutaneous tissue track 12 can be sufficiently filled without moving open distal end 36 of delivery tube 34 from the position as shown in FIG. 4. However, in some cases it may be desired to permit open distal end to be moved back out through tissue track 12 as material 30 is injected into the tissue track. Because thread 8 locks distal end 36 adjacent to position 32, this can be achieved only by either moving barrier assembly 4, which may not be desired until reactions have occurred with hemostatic flowable material 30 to create an effective plug, or by severing thread 8. One way to sever thread 8 would be to include a cutout or notch at distal end 36 of tube 34 so that the user could catch the end of thread 8 within the cutout or notch and then rotate assembly 6 until the thread is severed. At this point, open distal end 36 can be backed out of path 12 while maintaining barrier assembly 4 in place, thus back-filling tissue track 12.

Figure 5:
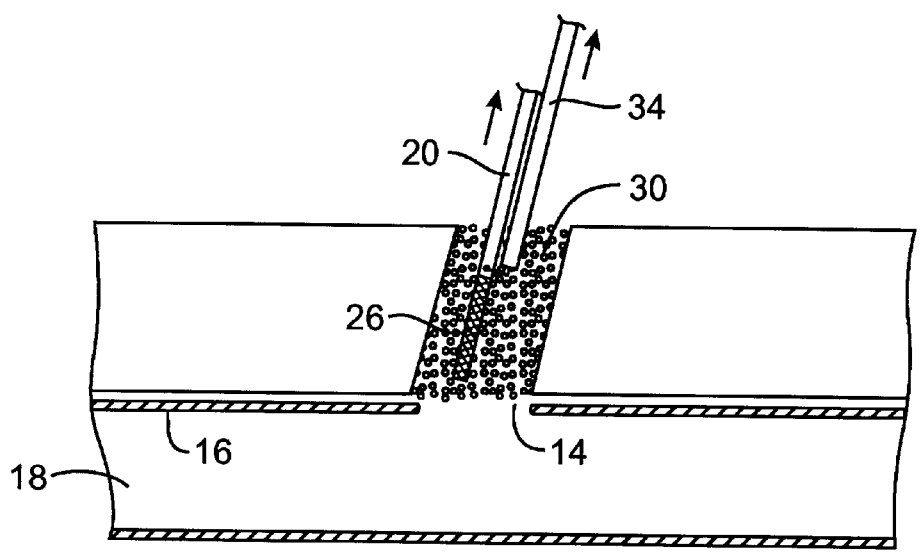
FIG. 5 illustrates the barrier assembly and delivery tube being withdrawn from the percutaneous tissue track after the percutaneous tissue track has been substantially filled with the hemostatic flowable material and the hemostatic flowable material has interacted with blood passing through the semipermeable barrier to effectively form a plug made of swollen flowable material and clotted blood.

After hemostatic flowable material has formed a plug or has reacted sufficiently with blood or one or more blood components to form an effective plug within tissue track 12, barrier actuator 22 is extended to move barrier 26 from the deployed configuration of FIG. 2 to the undeployed configuration of FIG. 1; barrier assembly 4 can then be withdrawn from tissue track 12 as suggested in FIG. 5. Any opening or gap which may be left by the retreating barrier carrier 20 and tube 34 will be quickly filled by hemostatic flowable material 30.

While the use of thread 8 as a delivery tube alignment device is simple and inexpensive, it may be desired to use different structure for accomplishing this. FIGS. 6–10 illustrate alternative embodiments with like reference numerals referring to like elements.

Barrier carrier 20A, see FIG. 6, includes at least two delivery guides 46 which guide the movement of delivery tube 34A along barrier carrier 20A. Delivery tube 34A includes a stop 48 which engages the proximal-most guide 46 when the open distal end 36 of delivery tube 34A is properly aligned at the distal end 28 of barrier carrier 20A.

FIG. 7 illustrates a different type of guide element in which barrier carrier 20B includes a slide opening 50 and delivery tube 34B includes a complementary, T-shaped slide 52. Delivery tube 34B would preferably include a stop element similar to stop 48 of FIG. 6; such a stop element is not shown in FIG. 7. FIG. 8 illustrates an alternative embodiment of the structure of FIG. 7 in which slide opening 50C is formed in delivery tube 34C, rather than as a part of barrier carrier 20B, and slide 52C is formed as an extension of barrier carrier 20C. The fit between slide opening 50C and slide 52C may be relatively tight so that substantially no hemostatic flowable material can flow through the gap between the two. Alternatively, a portion of the length of engagement of slide opening 50C and slide 52C can be made to be a somewhat loose fit to permit hemostatic flowable material 30 to pass between the two in addition to flowing out of the open distal end of delivery tube 34C. Backing out, back-filling movements of the delivery tube are facilitated through the embodiments of FIGS. 6, 7 and 8. FIG. 9 illustrates three alternatively-shaped slides 52D, 52E and 52F which could be used with embodiments similar to the embodiments of FIGS. 7 and 8.

FIG. 10 illustrates an embodiment in which the barrier carrier and delivery tube are incorporated into a combination tube 56. Combination tube 56 includes a main lumen 58, through which flowable material 30 passes, and a supplemental lumen 60, through which barrier actuator 22 passes. Instead of having a single flowable material exit at the open distal end of combination tube 56, tube 56 has a number of flowable material exits 62, 64 along at least part of its length;

this helps eliminate the need for backing the delivery tube out of tissue track 12 to back fill the tissue track with flowable material 30. Also, combination tube 56 acts as the barrier carrier alignment device to eliminate the need for thread 8 of FIGS. 1–5 and 11, markings 45 of FIG. 4, guides 46 and stop 48 of FIG. 6, and slide opening 50 and slides 52 of FIGS. 7–9.

FIG. 11 illustrates an embodiment in which the barrier carrier has been replaced by an elongate barrier carrier 20D. Barrier carrier 20D is solid but has a number of guide loops 66 extending from the barrier carrier along its length to guide barrier actuator 22.

Figure 12:
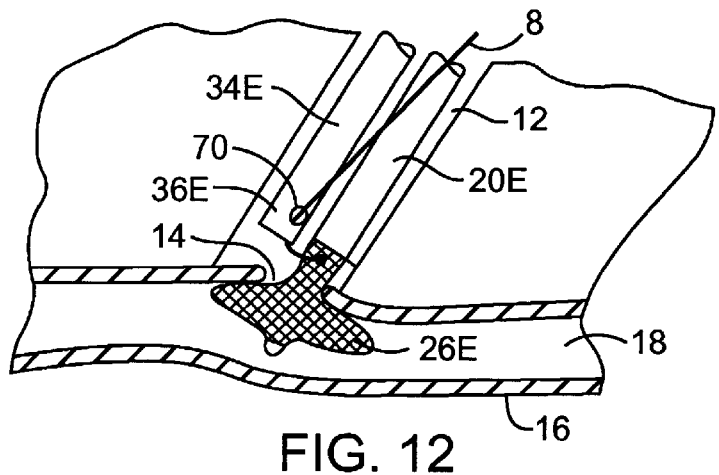
FIG. 12 is a view similar to FIG. 3 but with the thread passing out through a hole at the distal end of the flowable material delivery tube.

FIG. 12 illustrates a further embodiment in which thread 8 passes through the open distal end 36E of tube 34E and then through a hole 70 formed in tube 34E. This eliminates the need to sever thread 8 when it is desired to back-fill tissue track 12.

Figure 13:
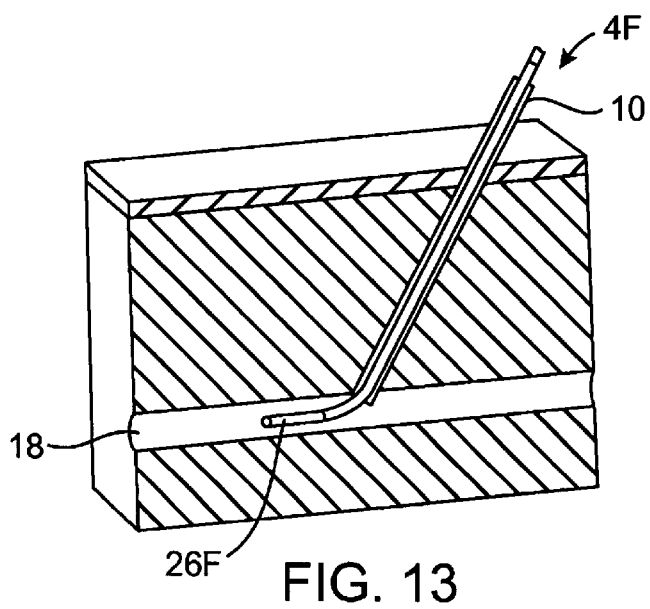
FIG. 13 illustrates an alternative embodiment of the barrier assembly of FIGS. 1–5 with the barrier within a blood vessel in a collapsed condition.
Figure 13A:
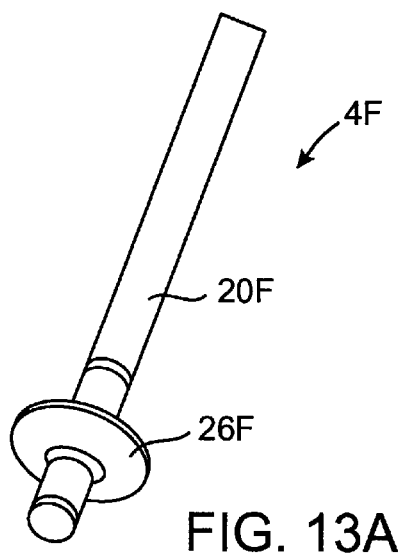
FIGS. 13A and 13B are enlarged views which show the distal end of the barrier assembly of FIG. 13 in a radially-expanded, deployed condition.
Figure 13B:
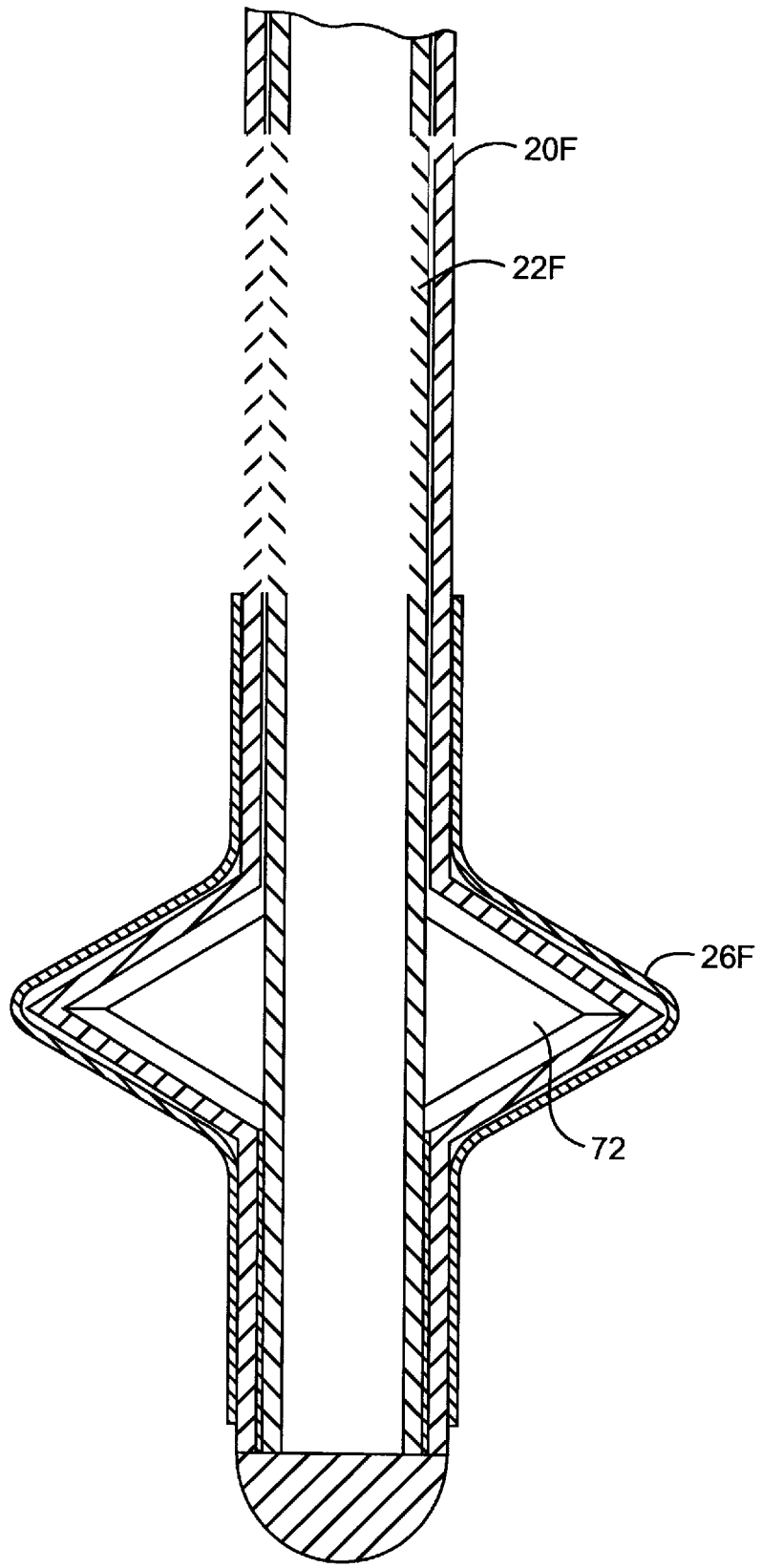

FIG. 13 illustrates a further barrier assembly 4F which uses, as shown in FIGS. 13A and 13B, an outer tube 20F as the barrier carrier and an inner tube 22F as the barrier actuator. Barrier 26F is mounted over the distal end of outer tube 20F. Outer tube 20F has a number, such as four, of axially-extending slits 72 located centrally beneath barrier 26F. Pulling inner tube 22F axially relative to outer tube 20F causes the slit region of the outer tube to buckle outwardly from the collapsed condition of FIG. 13 to the expanded, deployed condition of FIGS. 13A–13E.

Figure 13C:
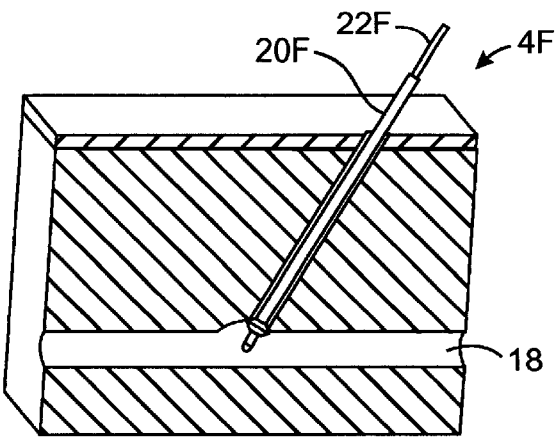
FIG. 13C shows the barrier assembly of FIG. 13 with the barrier in the deployed condition of FIGS. 13A and 13B and the introducer sheath removed.
Figure 13D:
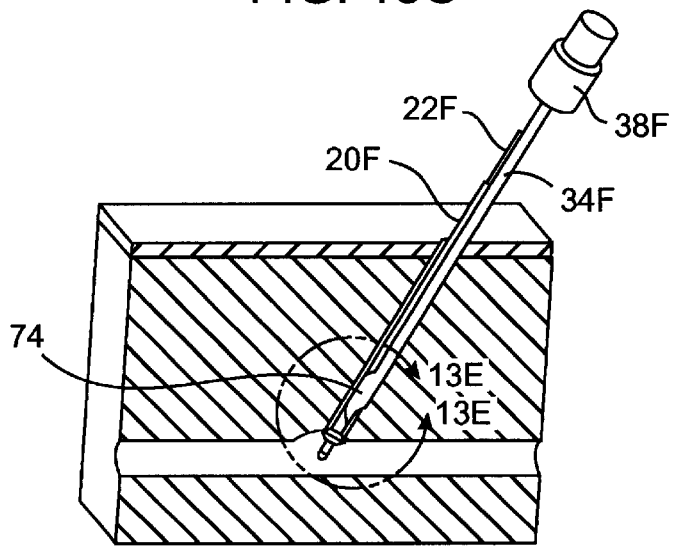
FIG. 13D shows the barrier assembly of FIG. 13C with the distal end of a flowable material delivery tube positioned adjacent the deployed barrier.
Figure 13E:
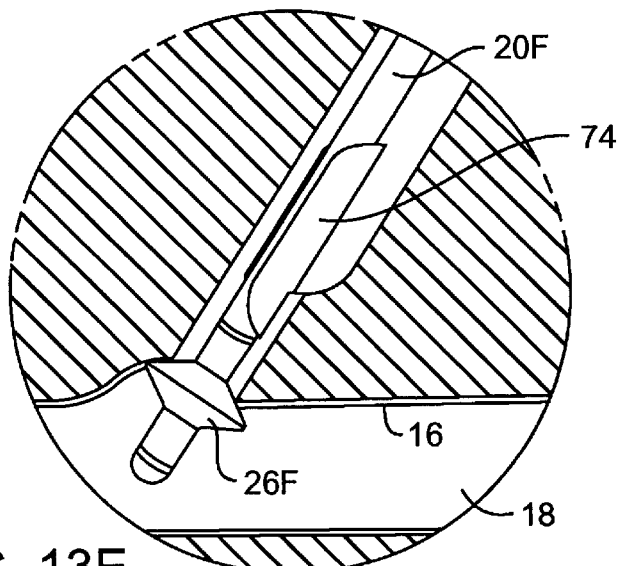
FIG. 13E is an enlarged view of the distal ends of the barrier assembly and delivery tube of FIG. 13D.

FIG. 13 shows barrier assembly 4F having been passed through introducer sheath 10 with barrier 26F within blood vessel 18. FIG. 13C illustrates barrier 26F in a deployed condition, pressed against the wall 16 of the blood vessel with introducer sheath 10 removed. FIG. 13D shows a delivery tube 34F having an integral tube clip 74, see FIG. 13E, at its distal end which clips to and slides along outer tube 20F. Fitting 38F can be coupled a source of hemostatic flowable material, such as a syringe.

Figure 14:
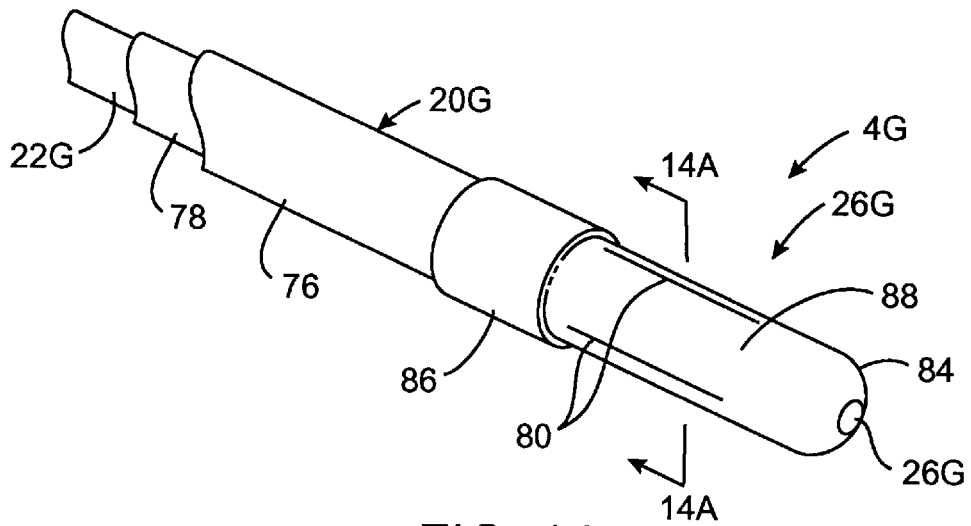
FIG. 14 is an enlarged isometric view of the distal portion of a further barrier assembly made according to the invention with the barrier in a collapsed configuration.
Figure 14A:
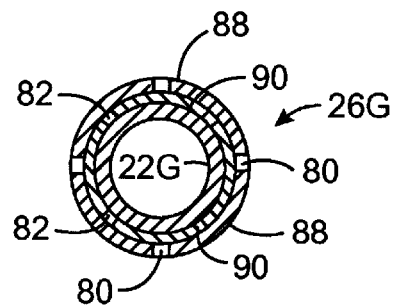
FIG. 14A is a simplified cross-sectional view taken along line 14A—14A of FIG. 14.
Figure 14B:
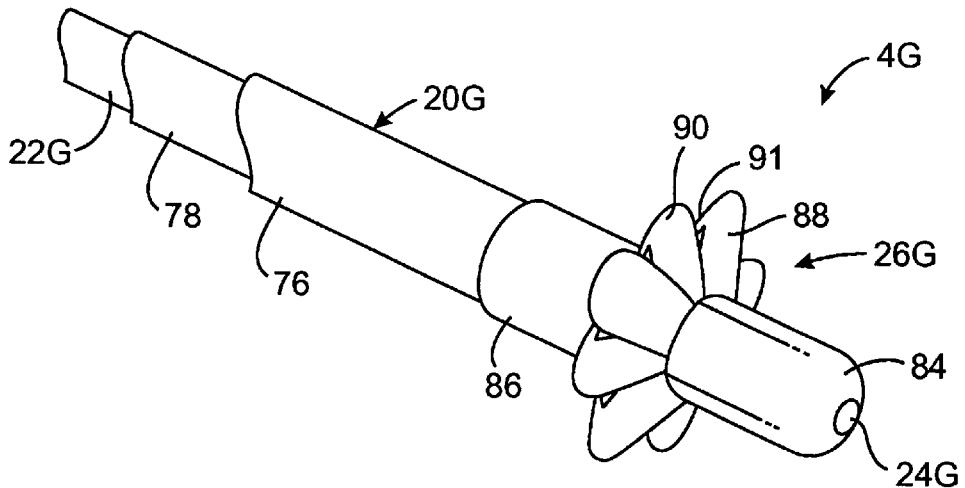
FIG. 14B illustrates the barrier assembly of FIG. 14 with the barrier in a laterally-expanded, fluid-flow-permitting configuration.

FIG. 14 illustrates the distal end of the further alternative embodiment of a barrier assembly 4G which is somewhat similar to the embodiment of FIG. 13B but differs primarily in that it does not include the semipermeable barrier 26F of the FIG. 13B embodiment. Barrier assembly 4 includes a barrier carrier 20G including a first, outer barrier carrier tube 76 and a second, inner barrier carrier tube 78. Tubes 76, 78 each have a series of four equally-spaced slits 80, 82, see FIG. 14A, at their distal ends. Slits 80, 82 are located between the tip 84 of barrier carrier 20G and a metallic stop ring 86, the use of which is described below. Tubes 76, 78 are free to move relative to one another in the area of slits 80, 82. However, tubes 76, 78 are prevented from any significant relative longitudinal or rotational movement so that by pulling on barrier actuator 22G, both tubes 76, 78 buckle in the region of slits 80, 82. This causes the laterally-expandable arms 88, 90 to buckle, that is deflected outwardly, to the deployed configuration of FIG. 14B. As seen in FIGS. 14A and 14B, slits 80, 82 are circumferentially offset so arms 90 of inner barrier carrier tube 78 extend through the opening created between the outwardly deflected arms 88 of outer barrier carrier tube 76. Laterally expanded arms 88, 90 create a number of fluid-flow-permitting gaps 91, see FIG. 4B. Gaps 91 are small enough to prevent flow of hemostatic flowable material 30 therethrough but large enough to permit passage of a suitable amount of blood into tissue track 12 for interaction with material 30.

FIG. 15 illustrates a further embodiment of the invention using barrier assembly 4G of FIG. 14. Barrier assembly 4G is housed within a spacer tube 92, the spacer tube being housed within a hollow delivery tube 34H. The distal end 94 of spacer tube 92 abuts stop ring 86 and is tapered to provide a smooth transition between barrier assembly 4G and delivery tube 34H as tube 92 is introduced into tissue track 12. Once in position within tissue track 12, barrier actuator 22G is pulled thus causing arms 88, 90 to be laterally expanded so that the barrier is in a deployed position. Spacer tube 92 is then partially withdrawn as shown in FIG. 15A to permit material 30 to be introduced into the generally annular flowable material path 96 defined between delivery tube 34H and barrier carrier tube 76. Flowable material 30 passes through a flowable material delivery port 98 at the proximal end of delivery tube 34H, along path 96 and out of the exit 99 of path 96. The embodiment of FIGS. 15 and 15A permits the flowable material to be properly introduced adjacent to barrier 26G and backfilled up into tissue path 12. After tissue track 12 is properly filled with material 30, spacer tube 92 and delivery tube 34H can be removed from barrier carrier 20G. When appropriate, barrier actuator 22G is pushed distally causing barrier 26G to move to the collapsed configuration of FIG. 14 to permit barrier assembly 4G to be removed from the tissue track.

FIGS. 16 and 16A illustrate a further embodiment of the invention incorporating barrier assembly 4G of FIG. 14 together with a laterally collapsible delivery tube 34I. Laterally-collapsible delivery tube 34I is mounted over outer barrier carrier tube 76 and defines a flexible, laterally-collapsible flowable material path 100 having an entrance 102 at a proximal end of path 100 and an exit 104 at a distal end of path 100 adjacent to barrier 26G. Material 30 is introduced into path 100 at entrance 102 through the use of a tube 106 having a fitting 108 at its proximal end coupleable to a conventional syringe or other supply of hemostatic flowable material 30. Tube 106 need not be inserted very far along path 100 of tube 34I to provide a sufficient seal between laterally-collapsible tube 34I and tube 106. In the preferred embodiment tube 34I is made of heat-shrinkable polyester; however, other materials, such as PET, PETG or PVC, could also be used. Path 100 is shown in FIG. 16A as being somewhat kidney-shaped. Other shapes for path 100 when laterally-collapsible tube 34I is in its expanded or extended condition can also be used. In this preferred embodiment, laterally-collapsible tube 34I is mounted over outer barrier carrier tube 76 through the use of an integral mounting sleeve 110 surrounding tube 76. If desired, other methods of mounting tube 34I to tube 76 could be used, such as through the use of an adhesive or heat bonding.

With the embodiment of FIG. 16, barrier assembly 4G with delivery tube 34I mounted thereto is typically deployed through an introducer sheath. The introducer sheath would then be removed, actuator 22G would be actuated to cause barrier 26G to be deployed, and material 30 would be introduced into percutaneous tissue track 12 using tube 106 inserted through entrance 102 of flowable material path 100. When it is time to remove barrier assembly 4G, barrier actuator 22G is pushed distally relative to tubes 76, 78 causing barrier 26 to move from the deployed configuration shown in FIG. 14B to the undeployed configuration of FIG. 14. Barrier assembly 4G and flowable material delivery tube 34I therewith can then be removed from tissue track 12.

Figure 17:
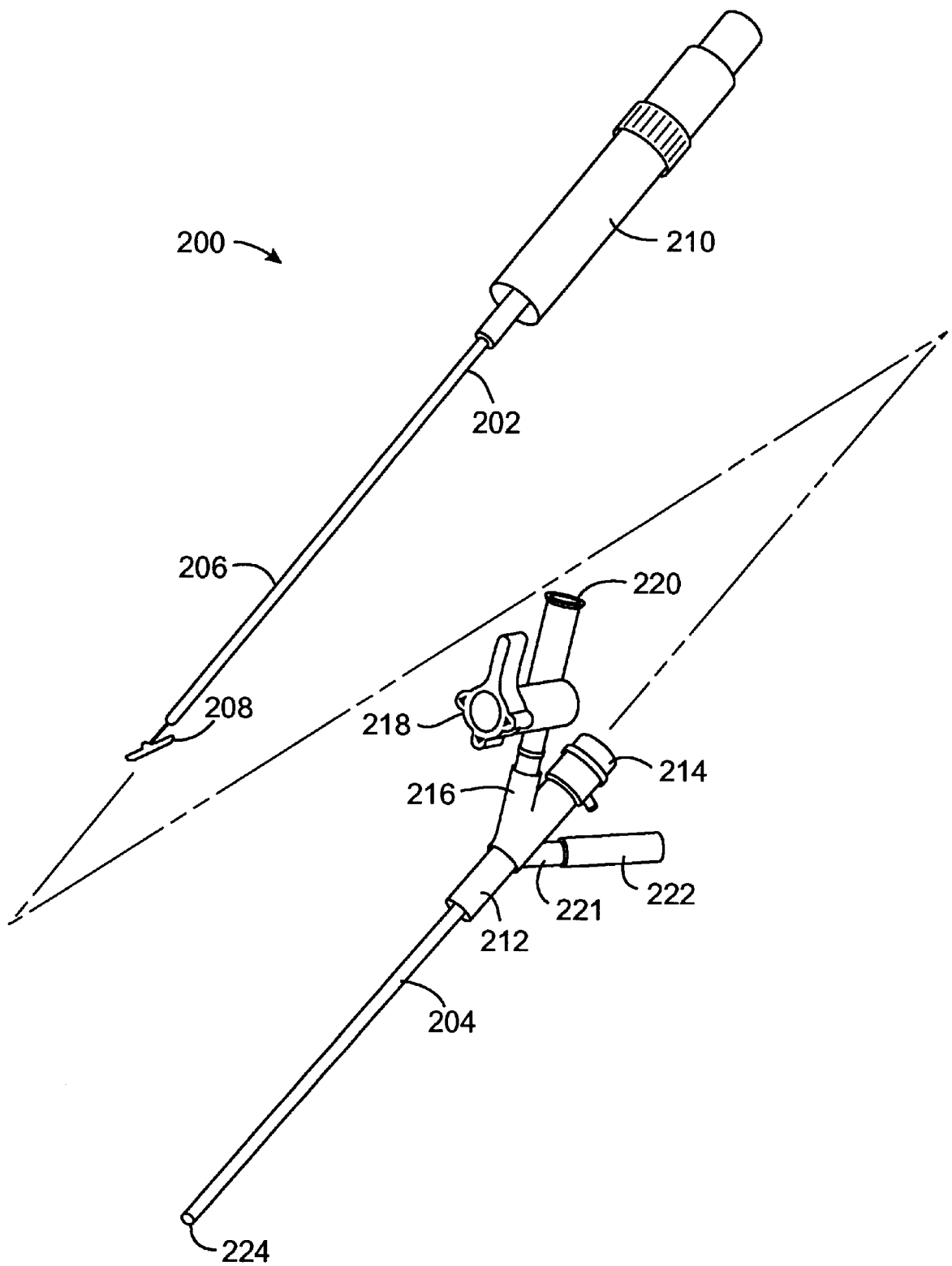
FIG. 17 illustrates an alternative system constructed in accordance with the principles of the present invention which comprises an elongate barrier carrier and a delivery tube.

Referring to FIG. 17, a system 200 for delivering a hemostatic gel to a vascular penetration in accordance with the principles of the present invention comprises an elongate barrier carrier 202 and a gel delivery tube 204. Barrier carrier 202 comprises a shaft 206 having an articulated foot 208 at a distal end thereof. The barrier carrier further comprises a handle 210 which is used to manipulate the carrier and foot, as described in more detail hereinafter. The drug delivery tube 204 includes a hub 212 at its proximal end. The hub 212 includes a primary port 214 having a hemostatic barrier to permit insertion of the shaft 206 of the barrier carrier 200 therethrough. Hub 212 also includes a second port 216 having a valve 218 and Luer or other suitable connector 220. The second port is intended for attachment of a syringe or other source of hemostatic gel to be delivered through the delivery tube 204. Additionally, hub 212 includes a blood reservoir 222 which is connected to the delivery tube 204 so that blood which enters the tube when its distal end 224 is positioned within a blood vessel lumen will pass into the reservoir and be visible to the user.

Figure 18A:
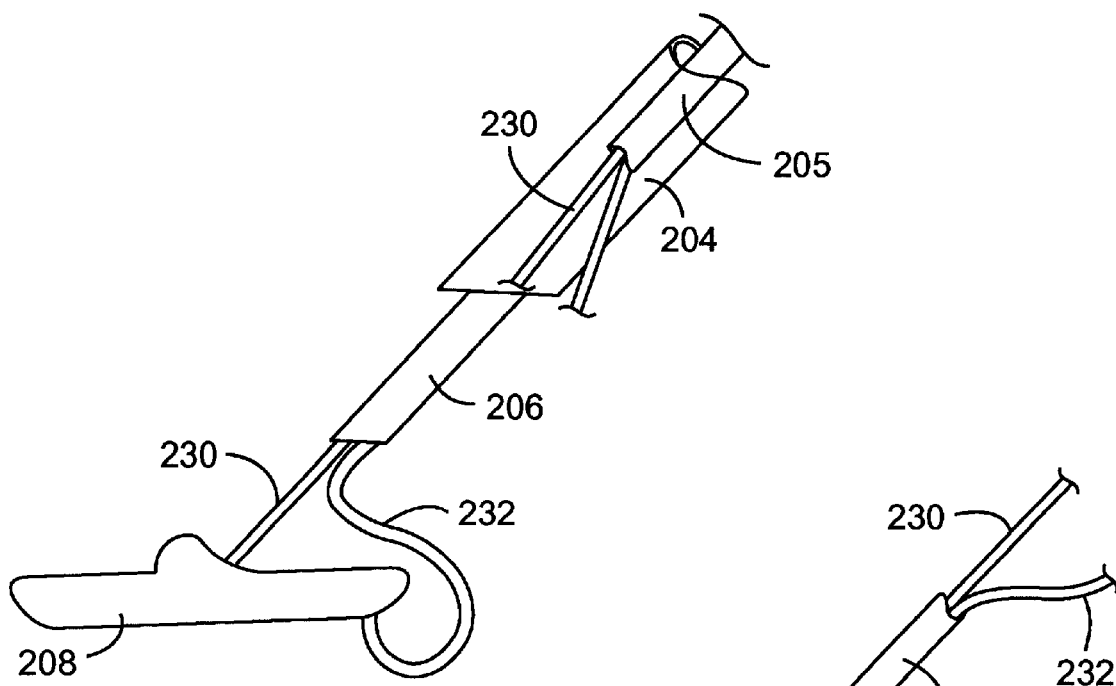
FIGS. 18A and 18B illustrate an exemplary barrier comprising an articulated foot having a blood flow passage therein.
Figure 18B:
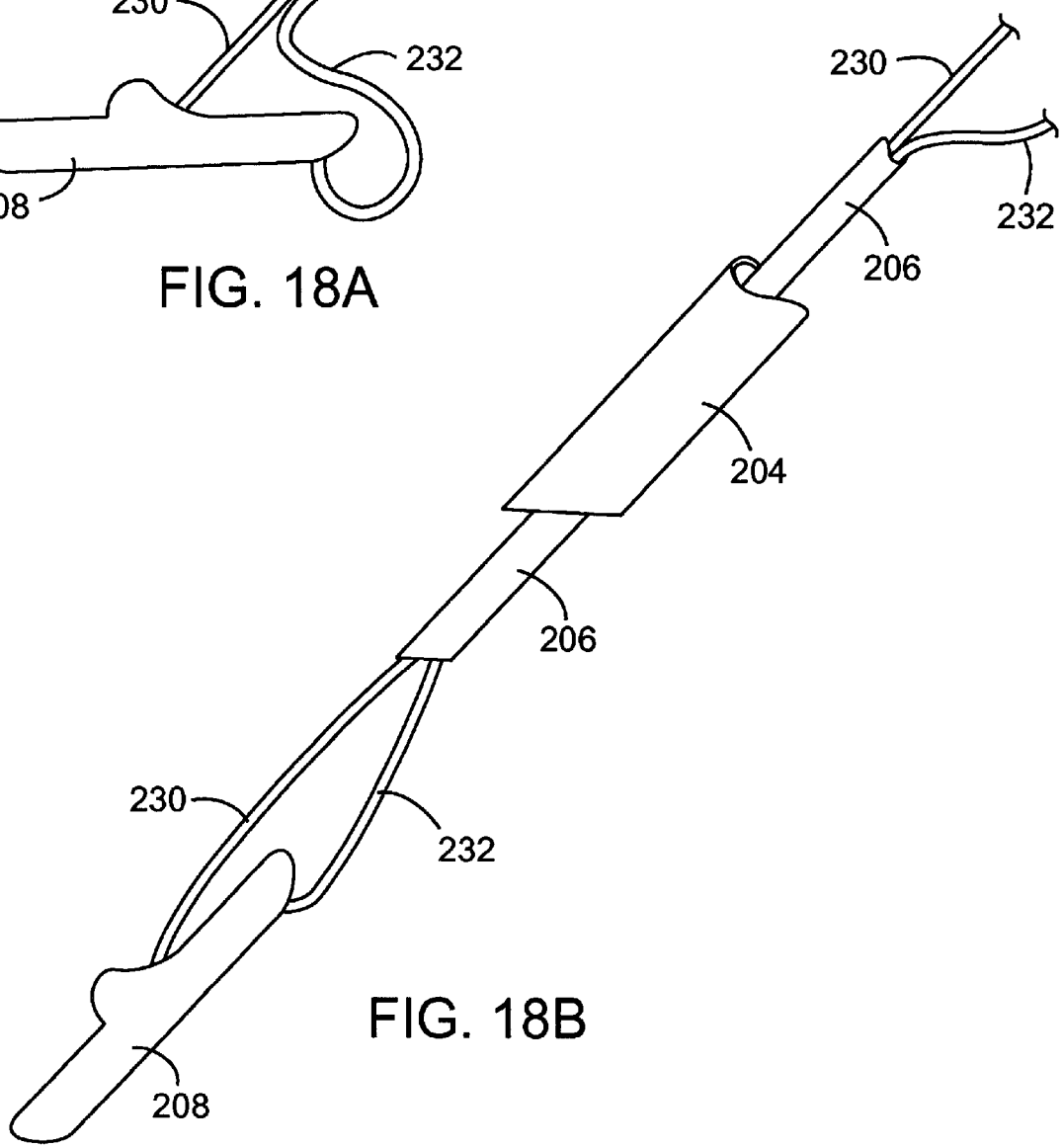

Referring to FIGS. 18A and 18b, articulated foot 208 is attached to the shaft 206 by a wire 230. The wire 230 will be sufficiently flexible and resilient so that the articulated foot 208 may be shifted between its deployed configuration, as shown in FIG. 18A, to its low profile or non-deployed configuration, as shown in FIG. 18B. For example, the foot 208 may be turned by applying tension with a filament 232, such as a length of suture, i.e. extending the wire in a distal direction from the hollow shaft 206, (e.g. as shown in FIG. 18B) or by alternatively retracting the filament 232 by pulling on the proximal portion thereof. Of course, a variety of other mechanisms for an articulated or pivotable attachment of the foot to the shaft 206 may be provided. Less simply, the foot could be attached to the shaft with an active hinge, e.g. having a pivot pin, a living hinge, e.g. run by weakening a region in the shaft and/or foot, or any other common mechanical connection which permits pivotable or articulated attachment of a component to a shaft. The articulated or pivotal connection should permit the foot to align itself with the posterior of the blood vessel as the foot is drawn in an anterior direction against the blood vessel wall, as described in more detail hereinbelow.

Figure 19:
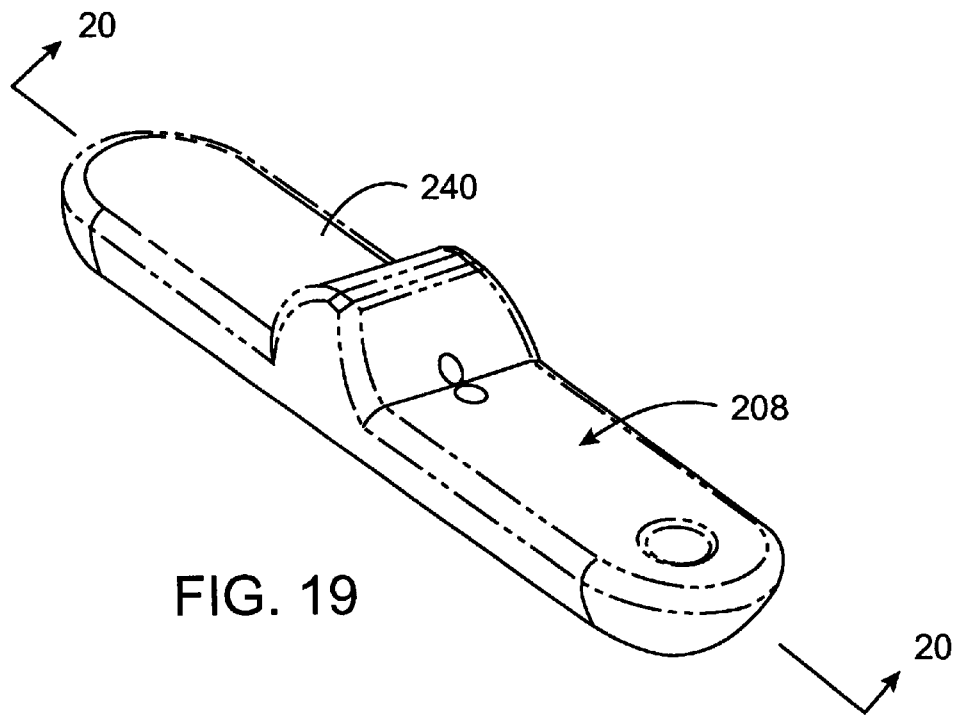
FIG. 19 is a detailed illustration of an exemplary barrier foot.
Figure 20:
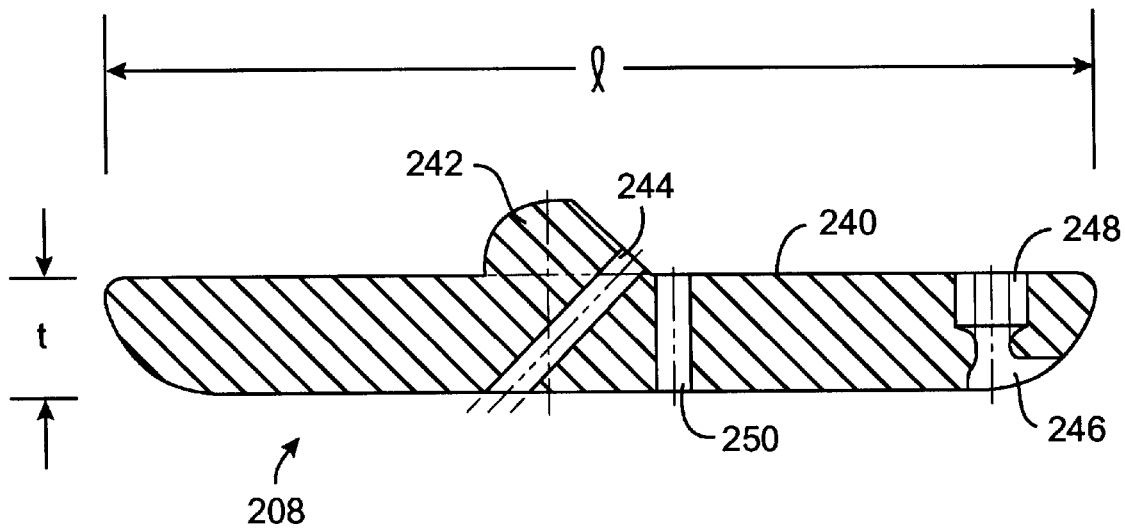
FIG. 20 is a cross-sectional view taken along line 20—20 of FIG. 19.

Referring now to FIGS. 19 and 20, an exemplary foot 208 will be described. For use with adult patients, the foot will generally have a length l in the range from 1 mm to 15 mm and a thickness t in the range from 0.1 mm to 5 mm. An upper surface 240 of the foot 208 will generally be flat but include the reinforced region 242 adjacent a bore 244 which receives the wire 230 (FIGS. 18A and 18B). A second bore 246 is provided for connecting the filament 232. For example, the filament 232 may include a ball or other large region at its distal end which is received in an enlarged portion 248 of the ball 246 with the suture then passing out through a lower portion of the bore. Finally, a third bore 250 is provided to permit the flow of blood through the foot while inhibiting the passage of the flowable hemostatic gel. The diameter of the passage will typically be cylindrical and have a diameter in the range from 0.02 mm to 0.5 mm, typically being about 0.1 mm.

Figure 21A:
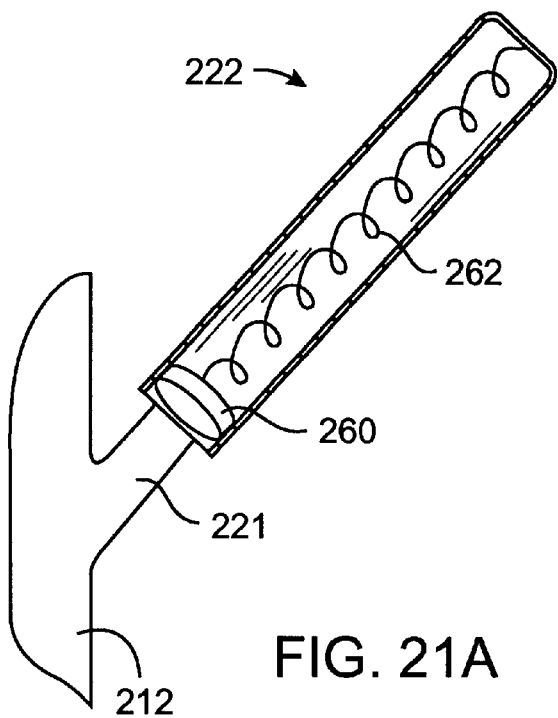
FIGS. 21A and 21B illustrate a blood collection reservoir constructed in accordance with the principles of the present invention.
Figure 21B:
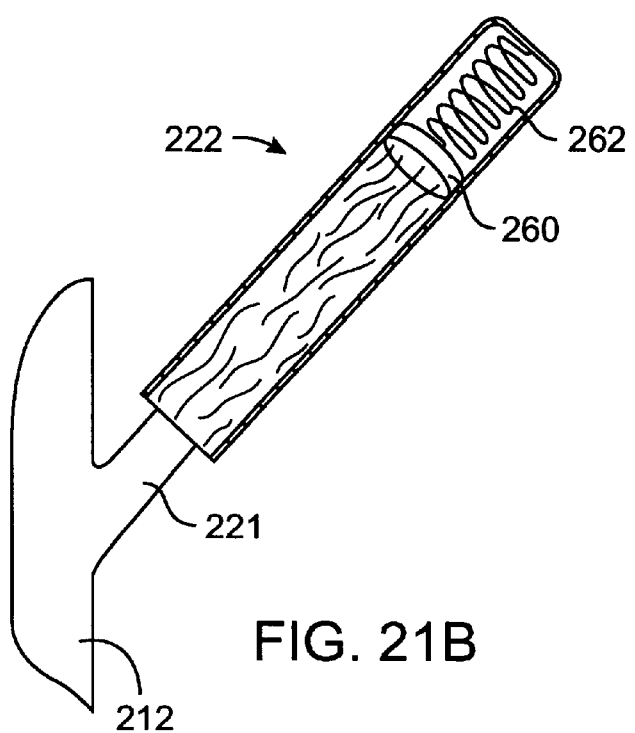

Referring now to FIGS. 21A and 21B, the blood reservoir 222 is connected to the hub 212 through the third port 221 which permits blood flowing upwardly through the gel delivery tube 204 to enter an anterior of the reservoir 222. At least a portion of the reservoir will be translucent or transparent so that the user may visually observe the presence of blood entering the reservoir. In a preferred aspect of the present invention, the reservoir will contain a resilient wall or other component, typically in the form of a spring-loaded piston 260, a spring 262 is selected to have a spring constant which provides a force which allows the piston to be compressed of blood at normal arterial pressures, e.g. in the range from 30 mm Hg to 120 mm Hg. When the distal end 224 of delivery tube 204 is in the presence of arterial blood, the blood will fill the interior of the reservoir 222 and compress the piston and spring assembly 260 and 262, as shown in FIG. 21B. As arterial blood pressure pulses, the position of the piston 260 will reciprocate within the reservoir 220, thus permitting the user to confirm that the distal end 224 of the delivery tube 204 remains in the target artery. Once the distal end 224 of delivery tube 204 is removed from the target artery, either intentionally or accidentally, the force of spring 262 will cause the piston 260 to compress against the blood and cause the blood to return through the hub 212 into the delivery tube 204. This both alerts the user to the fact that the distal end 224 has been removed from the artery and returns blood to the tissue tract which may be beneficial when combining with the delivered hemostatic gel.

Figure 22:
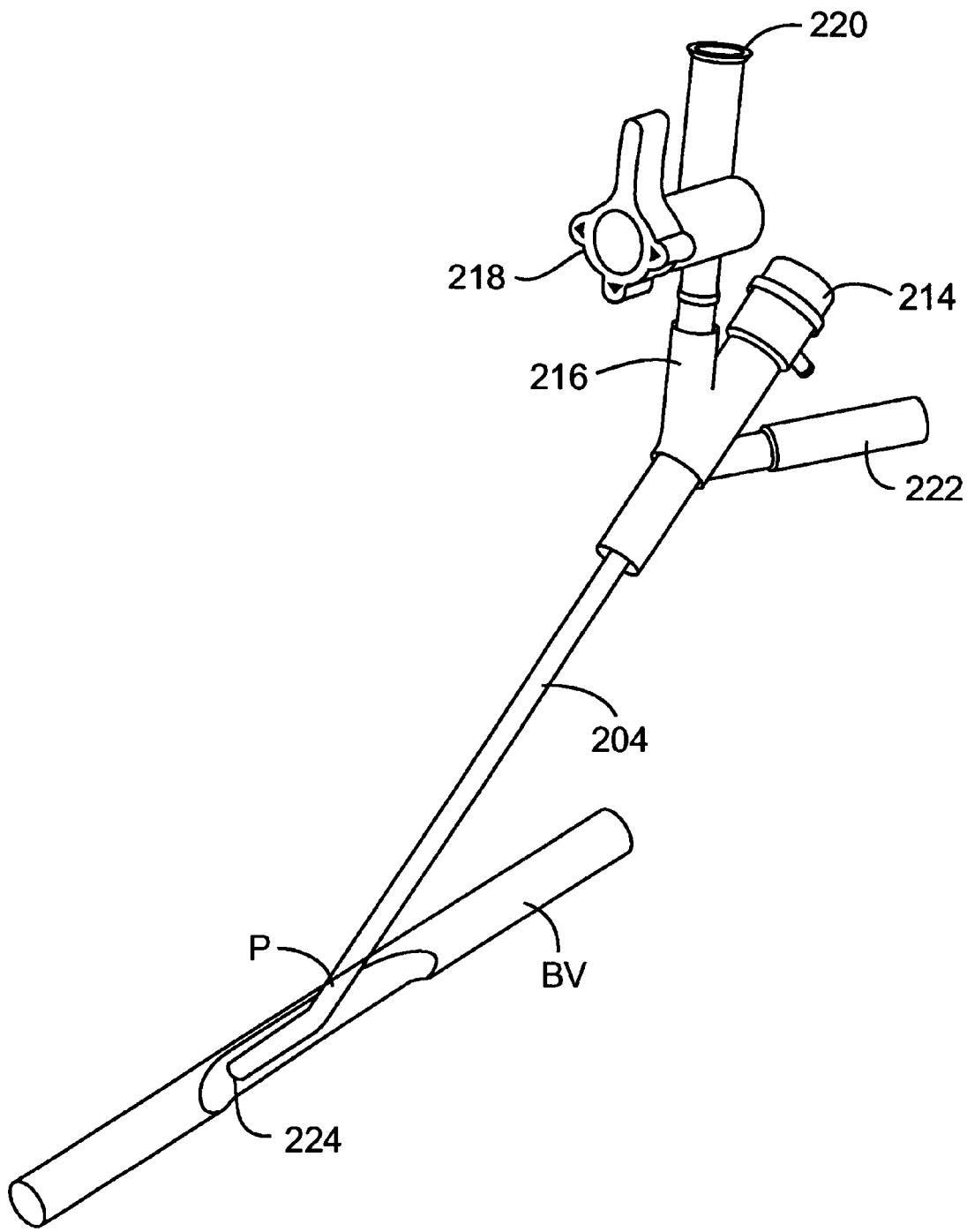
FIGS. 22–29 illustrate use of the system of FIG. 17 for sealing a vascular penetration according to the methods of the present invention.

Referring now to FIGS. 22–29, use of the system 200 for delivering a hemostatic gel to a vascular penetration will be described. Usually, a patient about to undergo a vascular sealing protocol according to the present invention will have recently completed an angiogram, angioplasty, or other percutaneously accessed intravascular procedure. The patient will have a standard introducer in place with a guide wire passing through the introducer into the vascular lumen. As shown in FIG. 22, the barrier carrier 202 is exchanged over the guide wire (not shown) for the standard introducer (not shown). The guide wire is then removed, leaving the barrier carrier 200 in place through the vascular penetration P in the wall of the blood vessel (BV). The blood vessel BV shown in FIGS. 22–26 includes a portion of the wall broken away so that the position of the distal end 224 of the tube may be observed within the blood vessel lumen.

As shown in FIG. 22, distal end 224 of the delivery tube 204 is in place within the blood vessel BV lumen and thus is exposed to blood at arterial pressures. Thus, the blood vessel reservoir 222 will fill with blood as shown in FIG. 21B above. Moreover, the pressure of the blood will be pulsing so that the piston 260 reciprocates, indicating that the distal tip 224 remains in place.

Figure 23:
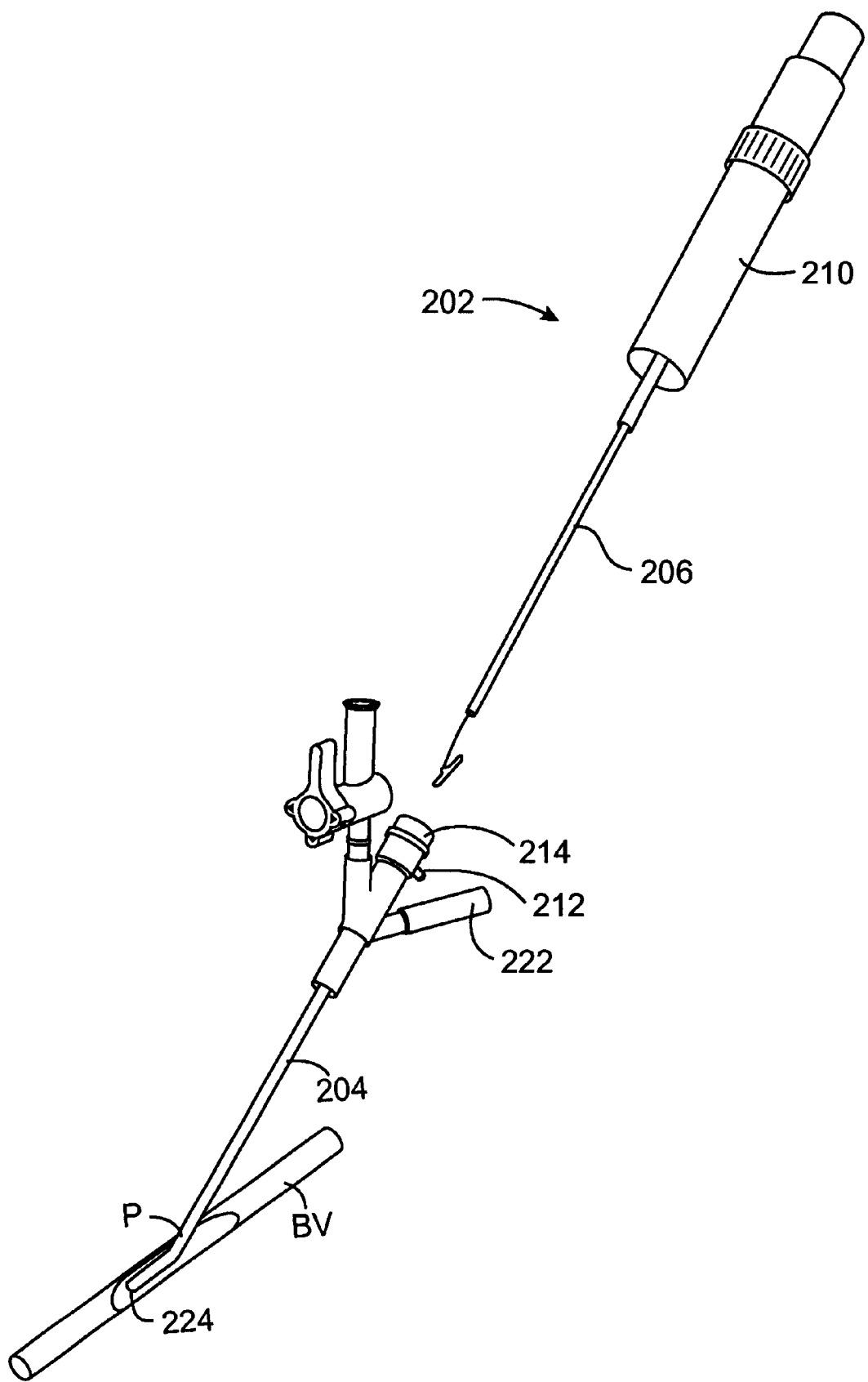

After it has been confirmed that the distal end 224 of the delivery tube 204 is in place and unobstructed by internal vascular structures, the barrier carrier 202 will be introduced through the gel delivery tube 204 by passing the articulated foot 208 and shaft 206 through the hemostatic port 214. The foot 208 is passed through the tube 204 until the foot 208 emerges from the distal end 234 of the delivery tube, as shown in FIG. 23. At the time the foot 208 first emerges, the delivery tube 204 will be positioned several centimeters through the vascular penetration P so that the foot is positioned fully within the blood vessel BV lumen and not engaged against the lumen wall near the penetration.

Figure 24:
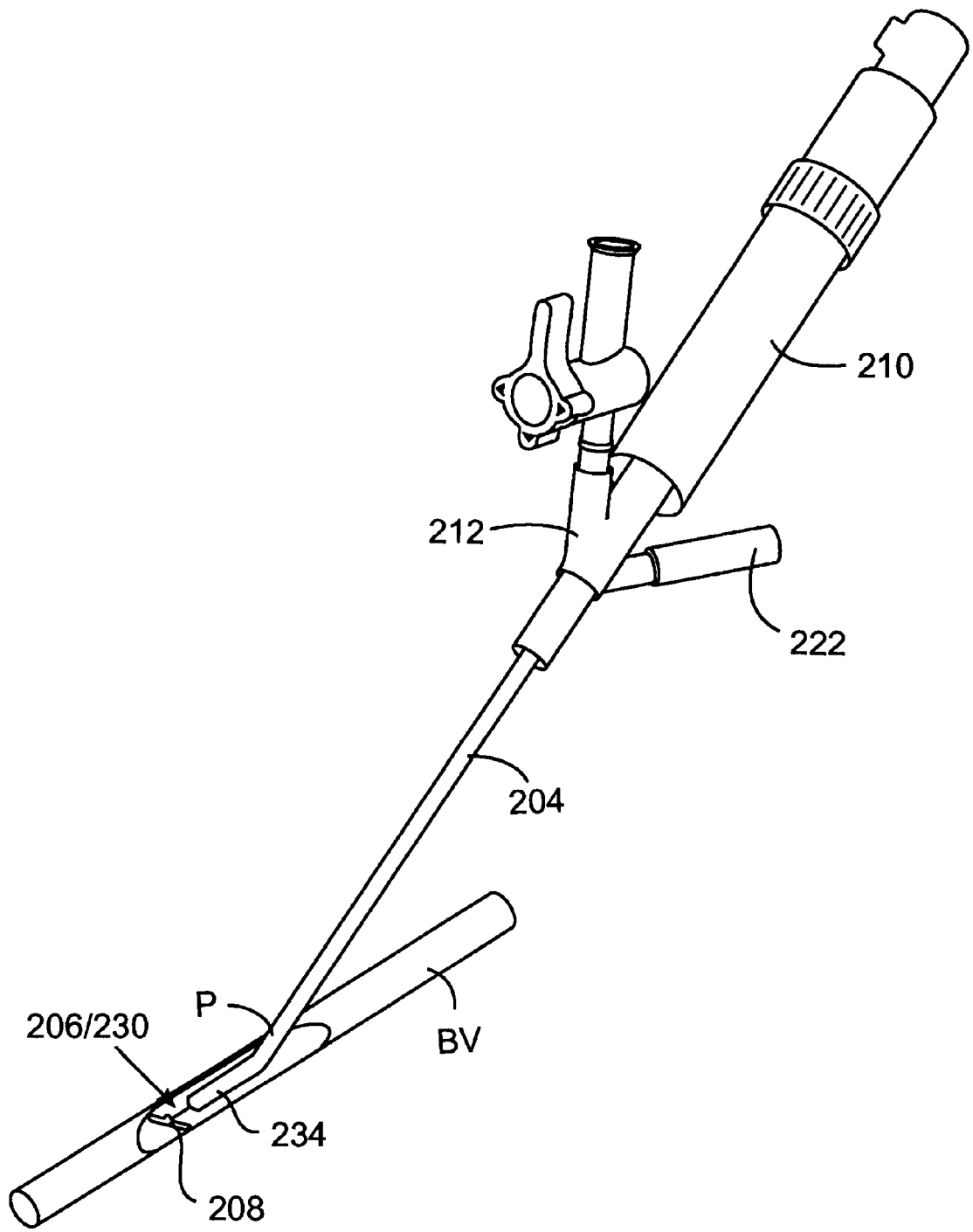
Figure 25:
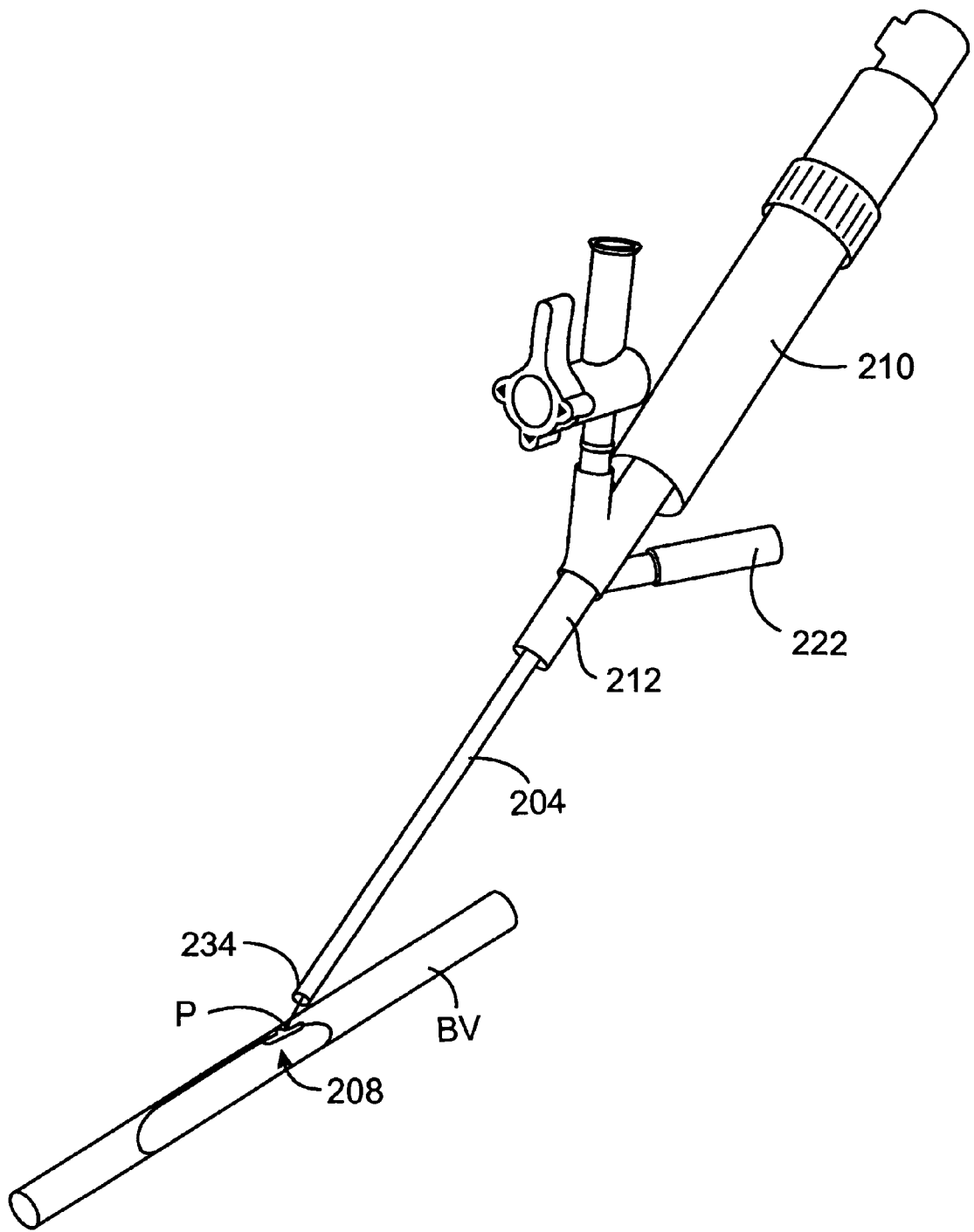

Once the foot 208 has been introduced into the blood vessel lumen and advanced beyond the distal end 234 of the delivery tube 204, the entire assembly of the delivery tube 204 and barrier carrier 202 may be manually drawn in a proximal direction so that the tube is pulled back against a posterior surface of the vascular penetration p as shown in FIG. 24. At this point, the vascular penetration will be temporarily "closed" by the foot which extends across the entire area of the penetration and is generally sealed against the blood vessel wall by a continuing proximal tension placed on it by the treating clinician. A small amount of blood, of course, may enter the tissue tract through the bore 250 (FIG. 20) in the foot, but blood flow will be very small and the blood pressure within the tissue tract which eventually reaches the blood reservoir 222 will be substantially cut off. At this point, the spring-loaded piston 260 will cause the blood in reservoir 222 to be returned to the tissue tract through the distal end 234 of delivery tube 204.

Figure 26:
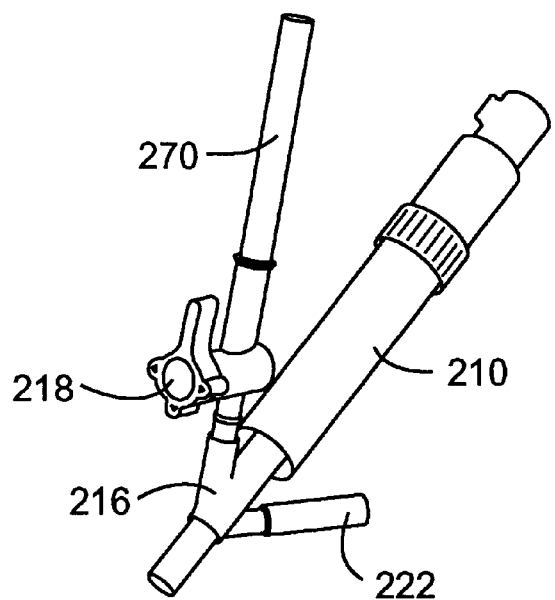
Figure 27:
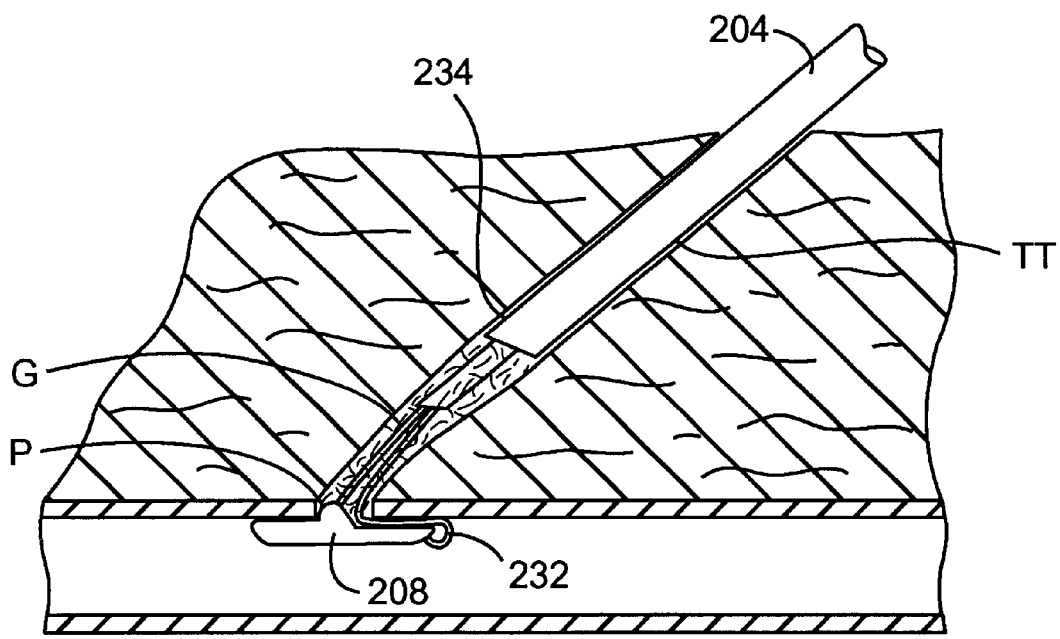

The patient is now ready to receive the hemostatic gel. As shown in FIG. 26, a syringe carrying the hemostatic gel may be attached to the second port 216 by connection to Luer 220. After the syringe is connected, the valve 218 may be opened, and the hemostatic gel delivered by depressing plunger 272 of syringe 270 to cause the gel to flow through the Luer tube 204 into the region over the outside of the penetration P as shown in FIG. 27. Gel G will mix with the blood which flows upwardly through the passage in foot 208 as well as the blood which enters from other sources, including from the blood reservoir 222 as described above.

After several minutes, typically from 1 to 10 minutes, the hemostatic flowable gel will begin to coagulate and harden to form an effective seal over in the vascular penetration P as shown in FIG. 27. While the gel is hardening, the delivery tube will remain in the tissue tract TT and foot 208 will remain pulled back against the posterior side of the vascular penetration P.

Figure 28:
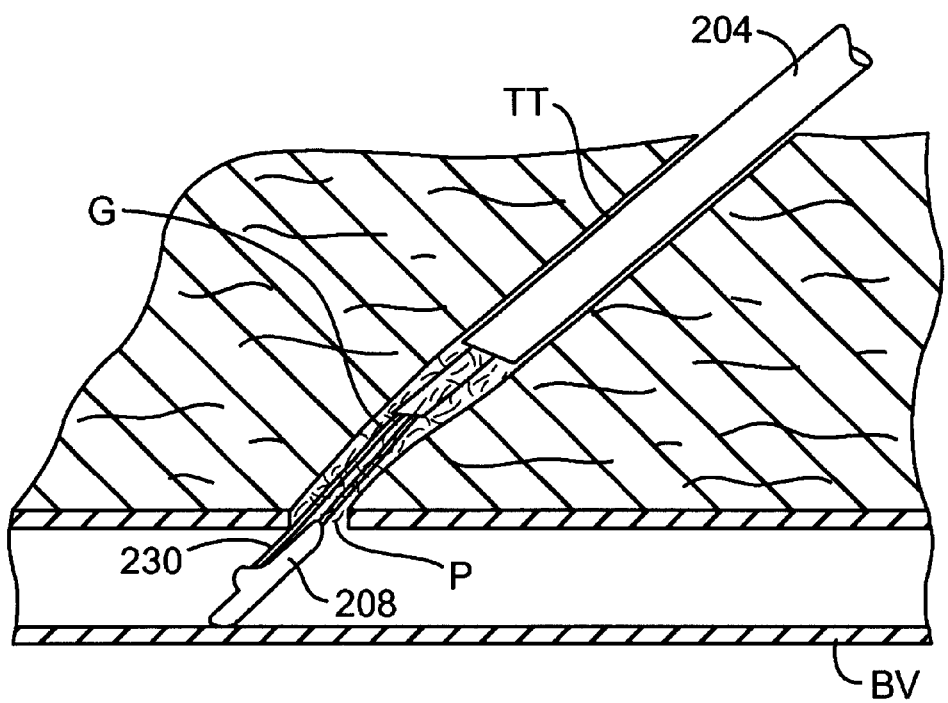

After the gel has hardened sufficiently, the foot 208 will be removed from the blood vessel BV lumen, as shown in FIG. 28. Usually, the foot will be extended by advancing wire 230 and tension will be placed on the suture 232 to rotate the foot, as shown in FIG. 28. Particular mechanisms within handle 210 for advancing and/or rotating the foot 208 are described in detail in prior application No. 60/212,181, the full disclosure which has previously been incorporated herein by reference. Such detailed mechanisms, however, do not form part of the present invention, and it will be appreciated that one skilled in the art could develop a wide variety of suitable mechanisms for reorienting the foot 208 in order to facilitate removal from the blood vessel BV lumen.

Figure 29:
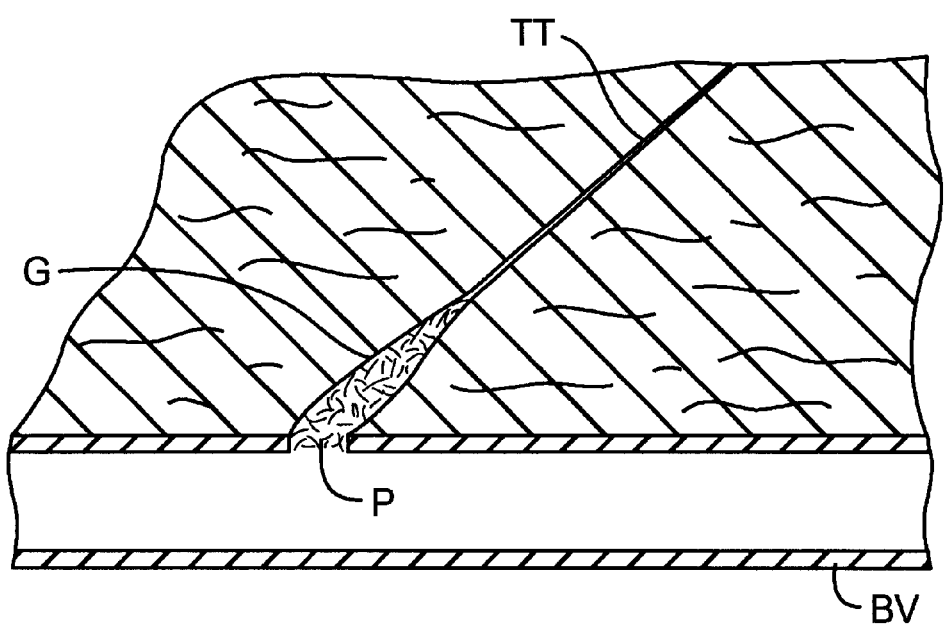

The foot is then removed by pulling back on the entire assembly of the barrier carrier 202 and gel delivery tube 204 so that the foot 208 passes through the penetration and through the hardening gel G. After the foot is removed, it may be useful to manually massage the patient over the penetration to cause any discontinuities in the gel to close. The gel will be sufficiently hardened, however, to inhibit and usually prevent any leakage of blood through the vascular penetration into the tissue tract, as shown in FIG. 29.

Figure 30:
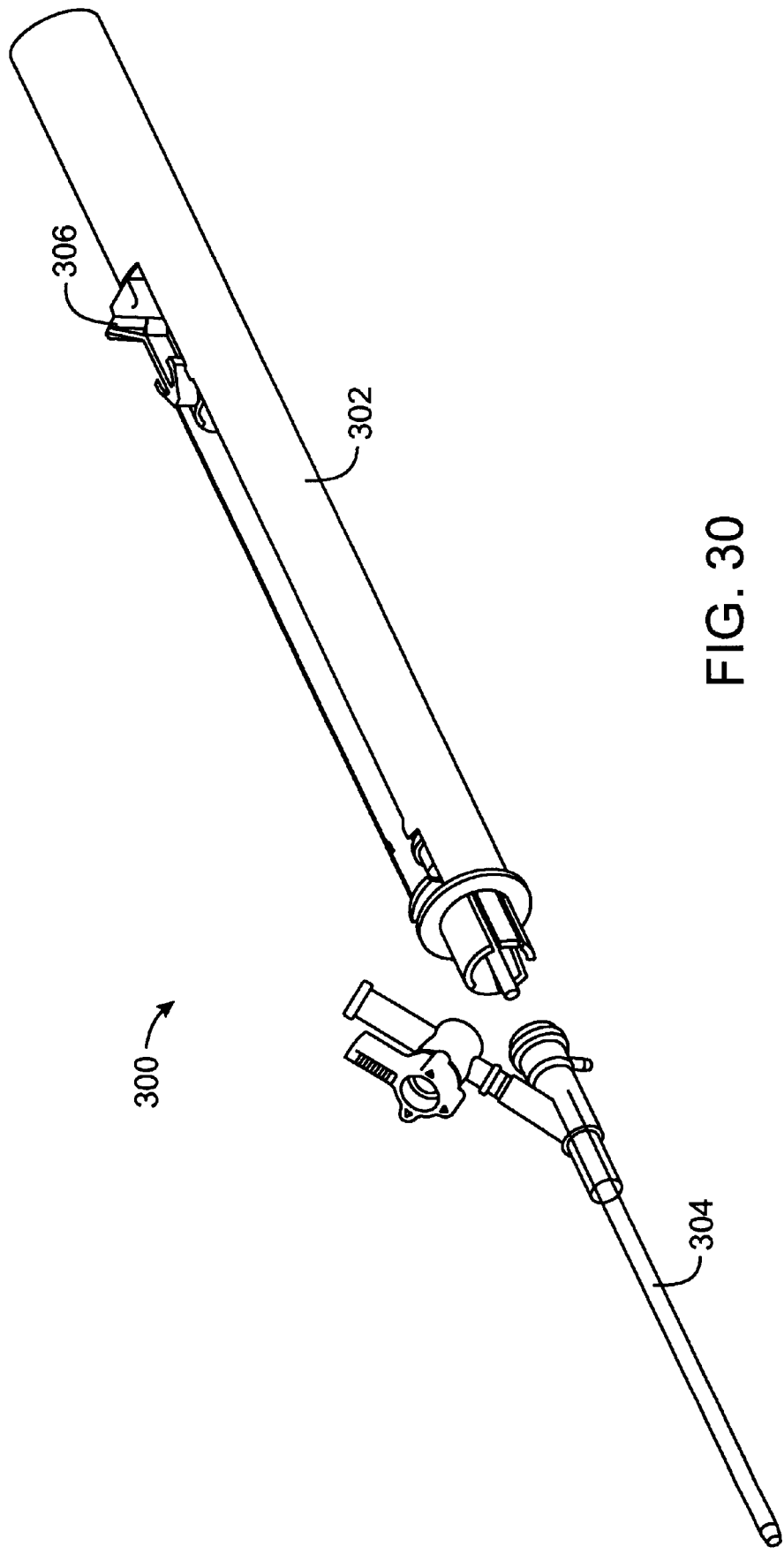
FIG. 30 illustrates a modification of the system of FIG. 17.

Various modifications may be made in the systems of the present invention without departing from the principles thereof. For example, a system 300 may include the barrier carrier 302 and gel delivery tube 304, as shown in FIG. 30. The gel delivery tube is substantially the same as gel delivery tube 204 described hereinabove, except that it lacks the blood reservoir 222. The barrier carrier differs in several significant aspects. In particular, the carrier includes a housing which covers the barrier, e.g. an articulated foot similar to foot 208. A mechanism permits the foot or other barrier to be advanced within the housing and into the delivery tube. Other mechanisms will permit advancement and retraction of the barrier, particularly to facilitate its removal from the blood vessel. The particular structure of systems similar to system 300 are provided in prior Application No. 60/212, 181, the full disclosure which is incorporated herein by reference.

Although the foregoing invention has been described in some detail by way of illustration and example, for purposes of clarity and understanding, it will be apparent to one skilled in the art that certain changes and modifications may be practiced within the scope of the appended claims.

What is claimed is:

1. A system for delivering a plug-forming material to an outside of a vascular penetration positioned at the end of a tissue tract over a blood vessel, said system comprising:

an elongate barrier carrier adapted to be positioned through the tissue tract and including a deployable barrier attached at a distal end of the carrier, said barrier inhibiting passage of the plug-forming material but permitting the passage of blood therethrough when deployed across the vascular penetration; and a delivery tube having a passage for flowing the plug-forming material, said delivery tube being simultaneously positionable in the tissue tract together with the barrier carrier to deliver the plug-forming material while the barrier is deployed across the vascular penetration.

2. A system as in claim 1, wherein the barrier comprises a porous, flexible structure.

3. A system as in claim 2, wherein the porous, flexible structure is a mesh.

4. A system as in claim 1, wherein the barrier comprises a solid structure having at least one passage bored therein.

5. A system as in claim 4, wherein the solid structure is pivotally attached to the distal end of the barrier carrier.

6. A system as in claim 5, wherein the barrier carrier further includes a mechanism for shifting the solid structure between a deployed configuration and a laterally closed position.

7. A system as in claim 1, wherein the barrier carrier is configured to pass through the passage of the delivery tube in a coaxial manner.

8. A system as in claim 1 or 7, wherein the delivery tube includes a blood reservoir on a proximal portion thereof, wherein said reservoir collects blood when a distal end of the delivery tube is in the blood vessel.

9. A system as in claim 8, wherein the presence of blood in the reservoir is visually discernable.

10. A system as in claim 8, wherein the reservoir includes a resiliently expandable structure which permits filling at arterial blood pressure and which empties the reservoir at a pressure below arterial blood pressure, whereby the blood can mix with the hemostatic gel which has been introduced through the delivery tube.

11. A method for delivering a plug-forming material to an outside of a vascular penetration positioned at the end of a tissue tract over a blood vessel, said method comprising:

positioning a barrier on an inside of the vascular penetration; and delivering a flowable hemostatic gel including at least one component of the clotting cascade through the tissue tract on the outside of the penetration, wherein the material flows over the barrier;

wherein the barrier inhibits passage of the material gel into the blood vessel lumen but permits the flow of blood back into the tissue tract to promote clotting of the material.

12. A method as in claim 11, further comprising collecting blood through the tissue tract prior to delivering the flowable hemostatic gel and combining the blood with the hemostatic gel to further promote clotting.

13. A method as in claim 11 or 12, wherein positioning the barrier comprises positioning a semipermeable membrane.

14. A method as in claim 11 or 12, wherein positioning the barrier comprises positioning a solid barrier having at least one passage to permit blood flow while inhibiting the passage of the material gel.

15. A method as in claim 11 or 12, wherein at least one member of the clotting cascade comprises thrombin.

16. A method as in claim 15, wherein the thrombin is present in a collagen or gelatin gel moiety.

17. A method as in claim 11, wherein the material is a flowable hemostatic gel comprising a protein selected from the group consisting of collagen, gelatin, thrombin, and fibrinogen.

18. A method for delivering a plug-forming material to an outside of a vascular penetration positioned at the end of a tissue tract over a blood vessel, said method comprising:

positioning a barrier on an inside of the vascular penetration; and delivering a flowable hemostatic gel including at least one component of the clotting cascade through the tissue tract on the outside of the penetration, wherein the material flows over the barrier;

wherein the barrier inhibits passage of the material gel into the blood vessel lumen but permits the flow of blood back into the tissue tract to promote clotting of the material;

and collecting blood through the tissue tract prior to delivering the flowable hemostatic gel and combining the blood with the hemostatic gel to further promote clotting.

19. A method as in claim 18, wherein positioning the barrier comprises positioning a semipermeable membrane.

20. A method as in claim 18, wherein positioning the barrier comprises positioning a solid barrier having at least one passage to permit blood flow while inhibiting the passage of the material gel.

21. A method as in claim 19, wherein at least one component of the clotting cascade comprises thrombin.

22. A method as in claim 21, wherein the thrombin is present in a collagen or gelatin gel moiety.

23. A method as in claim 18, wherein the material is a flowable hemostatic gel comprising a protein selected from the group consisting of collagen, gelatin, thrombin, and fibrinogen.

* * * * *